United States Patent [19]
Demarest et al.

[11] Patent Number: 6,138,053
[45] Date of Patent: Oct. 24, 2000

[54] OPERATING PROCEDURES FOR AUTOMATED NEEDLE SORTING, SWAGING AND PACKAGING MACHINE

[75] Inventors: David Demarest, Parsippany; Michael G. Hodulik, Dunellen, both of N.J.; Timothy P. Lenihan, Morrisville, Pa.; John F. Blanch, Tinton Falls, N.J.

[73] Assignee: Ethicon, Inc., Somerville, N.J.

[21] Appl. No.: 08/877,431

[22] Filed: Jun. 17, 1997

[51] Int. Cl.⁷ .................................................. G06F 19/00
[52] U.S. Cl. .............................. 700/117; 700/112; 53/475
[58] Field of Search .......................... 29/430, 703, 711, 29/712, 713, 720; 53/475, 507, 508, 147; 427/510; 700/112, 117, 160, 302, 113, 114

[56] References Cited

U.S. PATENT DOCUMENTS

| | | | |
|---|---|---|---|
| 5,240,746 | 8/1993 | O'Connell Litteral | 427/510 |
| 5,487,216 | 1/1996 | Demarest et al. | 29/705 |

*Primary Examiner*—William Grant
*Assistant Examiner*—Steven R. Garland
*Attorney, Agent, or Firm*—Scully, Scott, Murphy & Presser

[57] ABSTRACT

Methods and systems for packaging surgical needles. In this system, a plurality of packages are indexed, by means of a package carrier, through a plurality of work stations, at which various operations are performed on the packages. In particular, at each work station, an operating device is moved from a home position to an operating position to perform an operation on the package: and after finishing the operation, the operating device is returned to the home positions. With all of the operating devices in their respective home positions, the package carrier can then be moved to index the packages forward. Each of the work stations generates a respective return home signal when the operating device of the work station returns to its home position. A determination is made as to whether return home signals have been generated indicating that all of the operating devices have returned to their respective home position; and, if such return home signals have all been generated, the package carrier is moved to move each package thereon to another one of the work stations.

20 Claims, 22 Drawing Sheets

OPERATING PROCEDURES FOR AUTOMATED NEEDLE SORTING, SWAGING AND PACKAGING MACHINE

BACKGROUND OF THE INVENTION

This invention generally relates to machines that are used to suture, swage and package surgical needles. More specifically, the invention relates to procedures for operating those machines, or for controlling various operations on those machines.

Machines have recently been developed that automatically suture, swage and package surgical needles; and, for example, such machines are disclosed in U.S. Pat. Nos. 5,568,593, 5,495,420 and 5,487,212. Generally, in the operation of these machines, unsutured needles are fed to the machines, and indefinite lengths of suture, taken from spools or other suitable supplies, are inserted into recesses or openings in the needles. The needles are swaged in the areas of those recesses or openings to secure the connections between the sutures and the needles, the sutures are cut to preset lengths, and the needles are packaged.

These machines have proven to be highly valuable, and they effectively produce large numbers of excellent quality, packaged, sutured needles. Moreover, these needles are produced very economically on a large scale, high speed, mass production basis.

These machines are quite complex. Each machine has a multitude of work stations; and, in operation, the needles, or groups of needles, are moved through the work stations, one station at a time, and each work station is used to perform one or more specific tasks. Each work station may itself be a comparatively complex assembly, or group of assemblies, of moving parts.

In addition, it is important that the operations of the work stations be coordinated so that each station completes its assigned task or tasks before the work product is moved to the next work station. Achieving this needed coordination is complicated by several facts. First, the machines operate at high speeds; and, for example, each station may have less than one second to perform a series of tasks. Second, over time, the length of time that a particular work station needs to complete its particular task or tasks may change due to, for instance, normal wear of the machine parts at the work station.

SUMMARY OF THE INVENTION

An object of this invention is to improve machines for suturing and packaging needles.

Another object of the present invention is to provide a station check before indexing a rotary dial of a needle packaging machine.

A further object of this invention is to provide a check to be sure that various items on a needle packaging machine are in predetermined positions before moving the needle package on the machine.

Another object of this invention is to inspect a package of sutured needles for suture hanging outside the package.

Still another object of the present invention is to inspect a package of sutured needles for needles protruding from the package.

An object of the present invention is to monitor grippers used to pull test sutured needles to determine if they timely return to predetermined positions.

These and other objects are achieved with a machine for automatically threading, swaging and packaging surgical needles. Generally, in the operation of the machine, a first mechanism is used to sutures the needles and to pull test the needles to determine if certain maximum and minimum pull test requirements are met. The sutured needles are then transferred to packages on a second mechanism, and that mechanism indexes the packages through a series of stations to complete the packaging of the needles.

In accordance with a first aspect of the invention, various checks are made at the packaging mechanism before that mechanism is operated to index the needle packages. In accordance with a second aspect of the invention, different items at the station used to pull test the needles, are monitored to determine if they return timely to predetermined positions. Also, check are made at the station at which the needles are transferred to the packages, to be sure that those items are in preferred positions before the packages are moved. In addition, a detector unit and procedure are employed to inspect the packages for sutures hanging outside the packages, and another detector unit and procedure are provided to inspect the packages for needles protruding from the packages.

Further benefits and advantages of the invention will become apparent from a consideration of the following detailed description, given with reference to the accompanying drawings, which specify and show preferred embodiments of the invention.

DETAILED DESCRIPTION OF THE PREFERRED EMBODIMENTS

Figure 1:
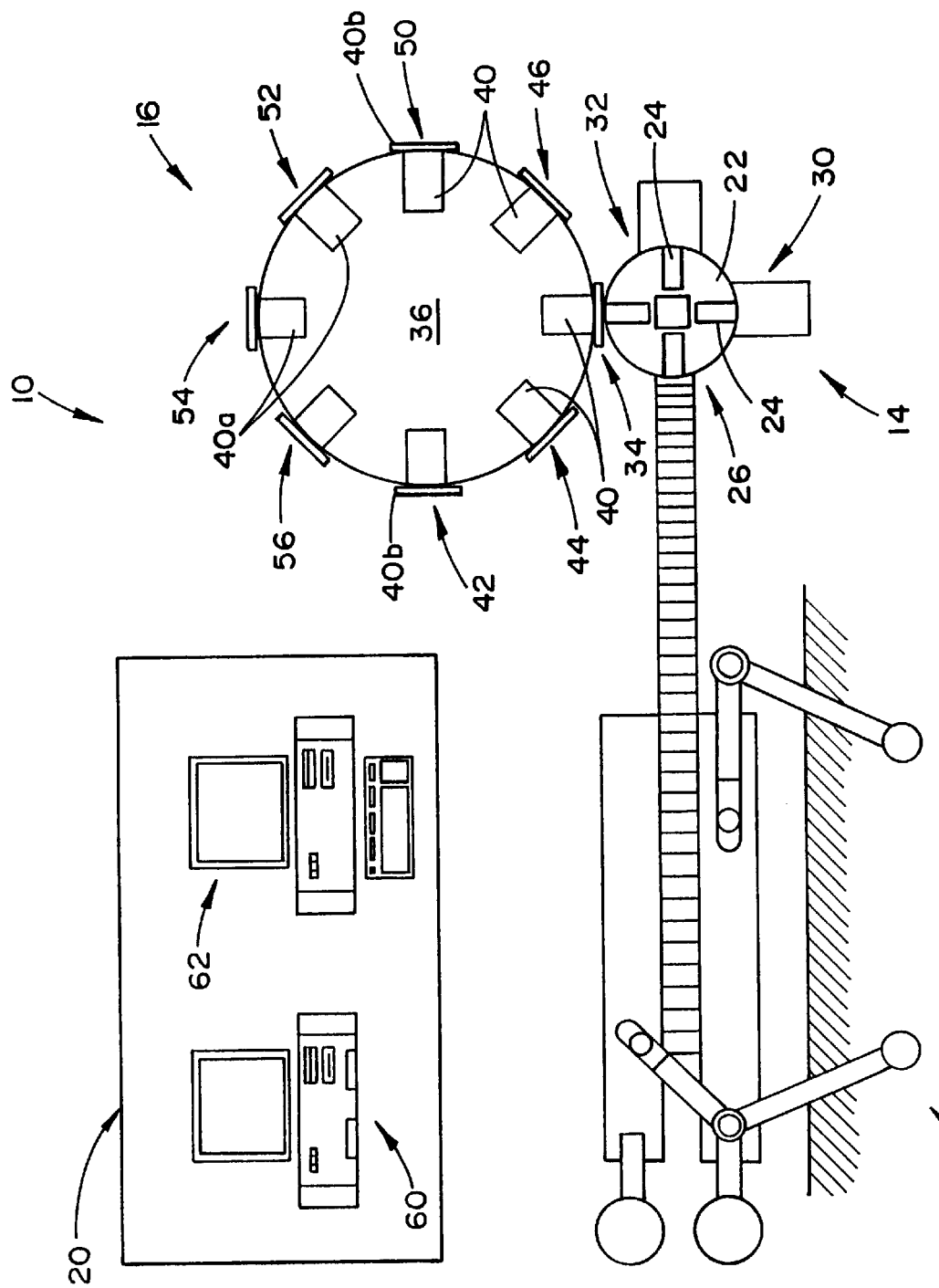
FIG. 1 shows an automated needle suturing and packaging machine.

FIG. 1 shows machine 10 for automatically threading, swaging and packaging surgical needles, and this machine comprises needle sorting and conveying mechanism 12, needle suturing and swaging mechanism 14, packaging mechanism 16, and control system 20. Mechanism 12 includes a rotatable dial or plate 22, a multitude of needle grippers 24 mounted on the plate, and a multitude of work stations 26, 30, 32 and 34 located around that dial or plate. Similarly, mechanism 16 includes a rotatable dial or plate 36, a multitude of package or tool nests 40 mounted thereon, and a multitude of work stations 42, 44, 34, 46, 50, 52, 54 and 56 located around the dial or plate. Control system 20 preferably includes operator computer 60 and supervisor computer 62.

With the preferred embodiment of machine 10 shown in FIG. 1, four grippers 24, referred to as multi-axis grippers, are mounted on plate 22 and are equally spaced therearound. Also, eight tool nests 40 are mounted on and are equally spaced around the circumference of plate 36. Each tool nest includes a housing or body 40a and an outward portion 40b. Body portion 40a is fixedly mounted on plate 36; and outward portion 40b projects outwardly beyond the circumferential edge of dial 36 and is designed to receive and to hold a needle package tray.

Figure 2:
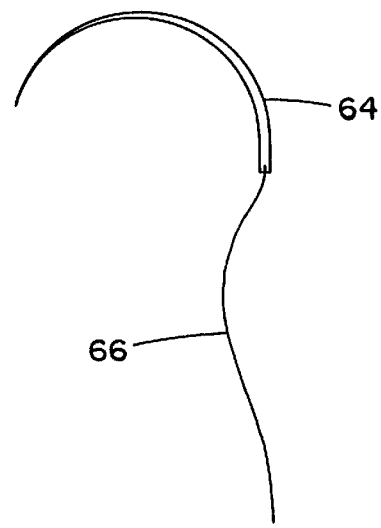
FIG. 2 shows a needle that has been sutured on the machine of FIG. 1.

Machine 10 may be used with a variety of types and sizes of needles. As an example, FIG. 2 shows a needle that has been sutured and swaged on the machine, with the needle and the suture being referenced at 64 and 66 respectively.

Figure 3:
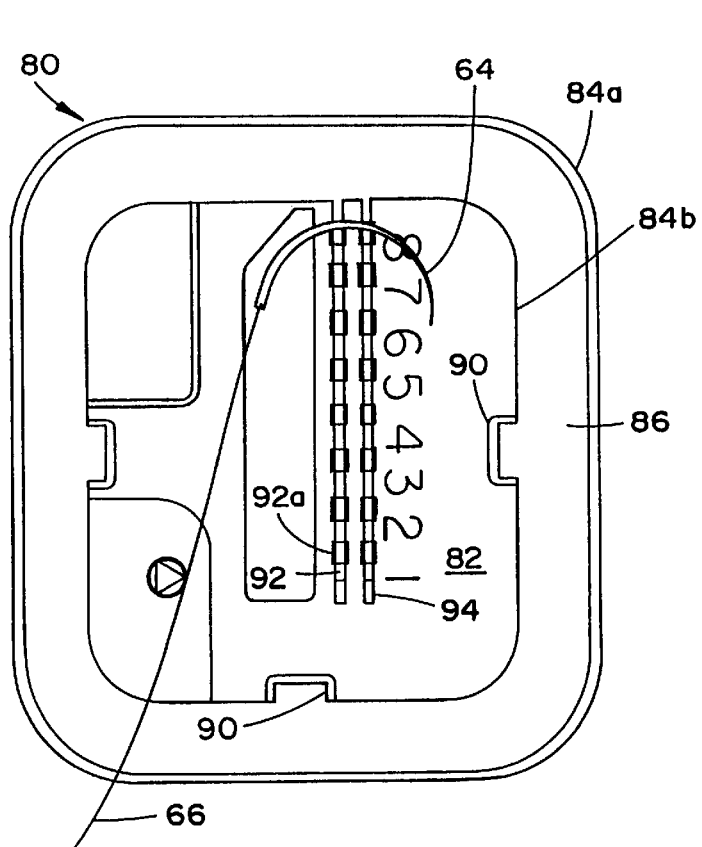
FIG. 3 is a plan view of a package tray that may be used on the machine of FIG. 1.
Figure 4:
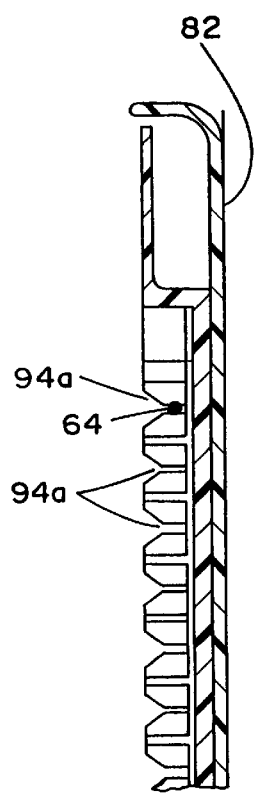
FIG. 4 is a cross-sectional view through a central portion of the package tray.

In addition, machine 10 may be used to package needles in a variety of types and sizes of packages; and, for example, one type of package or package tray that may be used on machine 10 is illustrated in FIGS. 3 and 4. Tray 80 has a planar base 82 of generally rectangular configuration. A pair of upstanding walls 84a and 84b form a channel 86 extending around the periphery of tray 80, and a plurality of suture retaining fingers 90 extend over that channel. A pair of inner upstanding members 92 and 94 form a multitude of gaps or notches 92a and 94a for receiving and holding needles.

Generally, in the operation of machine 10, mechanism 12 sorts, singulates and conveys precisely oriented surgical needles to needle grippers 24 on rotary dial 22. That dial then rotates, in the counterclockwise direction as viewed in FIG. 1, to move, or index, the needles to and through work stations 26, 30, 32 and 34 to suture and swage the needles. At work station 34, the needles are transferred from dial 22 to dial 36, which then rotates, also in the counterclockwise direction as viewed in FIG. 1, to move, or index, the needles to and through work stations 46, 50, 52, 54 and 56 to package the needles.

In the operation of machine 10, a plurality or a multitude of needles, such as eight needles, are placed in each needle package on packaging mechanism 16; and because of this, dial 22 is indexed or moved a plurality of times, such as eight times, each time dial 36 is moved or indexed. Moreover, in the operation of machine 10, operations are performed simultaneously at all of the work stations of the machine. In particular, during a given work cycle of mechanism 14, operations are performed at each of the work stations 26, 30, 32 and 34; and once those operations are completed, rotary dial 22 rotates to move the needles to the next work station. Similarly, as illustrated in the flow chart of FIG. 5, during a given work cycle of mechanism 16, operations are performed at each of the work stations 42, 44, 34, 46, 50, 52, 54 and 56; and once these operations are completed, rotary dial 36 usually rotates to move each package on the dial to the next work station.

More specifically, with reference to FIG. 1, at station 26, grippers 24 on dial 22 receive the needles, one at a time, from mechanism 12. Station 30 is an automatic swaging station, where suture material is inserted into the needle, swaged thereto, and cut; and station 32 is a pull test station, where the sutured needles, referred to as armed needles, are pull tested to determine whether certain minimum and/or maximum pull test requirements are met. Station 34 is a transfer station, where the armed surgical needles are transferred to a package tray mounted on rotary plate 36.

Station 42 of needle packaging mechanism 16 is a package load station, where an empty package tray 80 is mounted on a receiving nest 40; and station 44 is a package detect station, where a check is made to determine whether the package tray has in fact been mounted on the tool nest. Station 34 is, as mentioned above, a load station, where the armed needles are transferred from mechanism 14 onto the package tray on mechanism 16; and station 46 is a needle check station, where a check is made for missing needles.

Station 50 is a suture winding station where the trailing ends of the sutures of the armed needles in a package tray are gathered and wound around the package tray; and station 52 is a manual inspection station, where a manual inspection may be made of the work in progress. At station 54, a cover is applied to the package tray; and at station 56, the package is removed from the machine 10. The removed package may be further processed, or if the package has been found defective, the package may be discarded.

Control system 20 helps to supervise, control and coordinate the operations of mechanisms 12, 14 and 16. More specifically, supervisor computer 62 may be provided with various data bases, referred to as batch recipes, that contain lists of values for parameters on machine 10. Computer 62 may have a respective one batch recipe for each type of needle that may be used on machine 10; and when needles of a given type are fed to the machine, the associated batch recipe is invoked to set parameters on the machine. Also, supervisor computer 62 may hold data or status words that in turn hold bits or flags describing various conditions on machine 10. Some of these status words may indicate conditions at the work stations on the machine, and other status words may describe the conditions of the needles or of the packages at these stations.

Operator computer 60 acts as an interface between an operator and supervisor computer 62 for receiving input data and commands from the operator and for displaying data and messages to the operator. The operator computer also acts as an interface between the operator and sorting mechanism 12, suturing mechanism 14, and packaging mechanism 16.

Any suitable sorting and conveying mechanism, and any suitable suturing and swaging mechanism may be used in machine 10. Likewise, machine 10 may have any appropriate packaging mechanism and control system. Mechanisms and control systems that may be used in machine 10 are disclosed, for example, in U.S. Pat. Nos. 5,568,593, 5,495,420, 5,487,216, and 5,487,212, the disclosures of which are herein incorporated by reference. U.S. Pat. Nos. 5,487,216 and 5,487,212 also describe in detail a needle package that may be used on machine 10.

Figure 6:
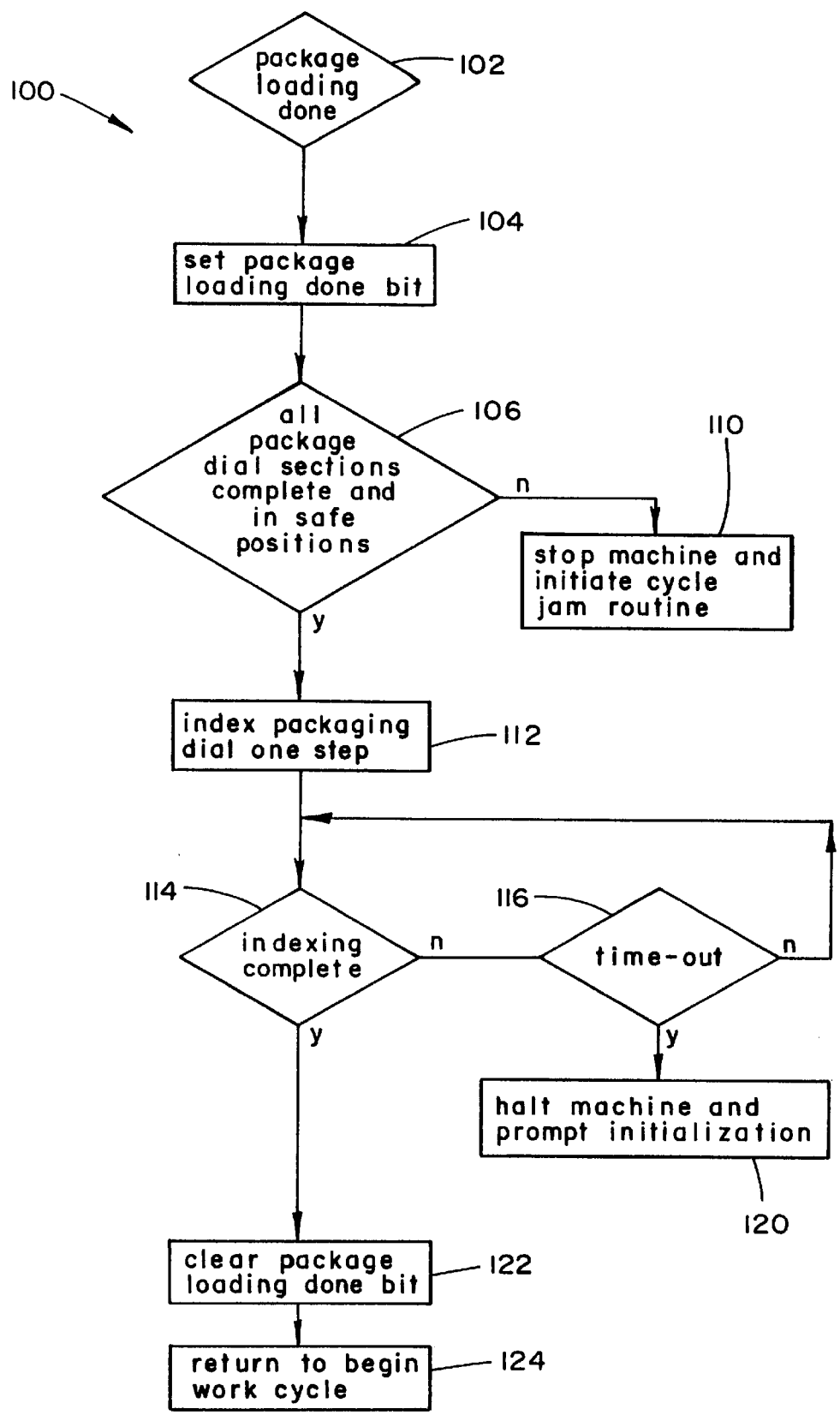
FIG. 6 is a flow chart of a procedure for indexing the packaging mechanism.
Figure 7:
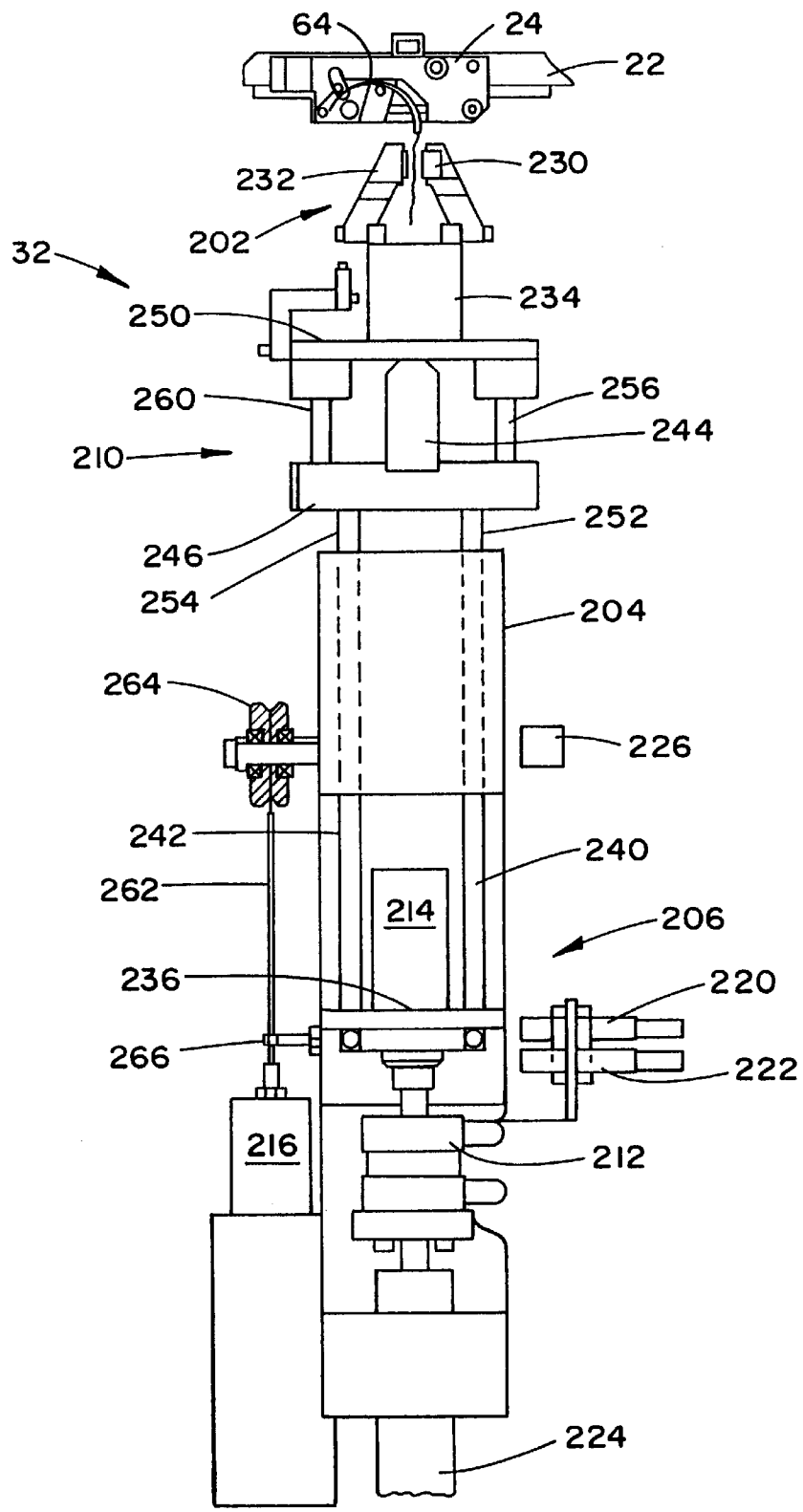
FIGS. 7 and 8 show a pull test station of the machine of FIG. 1.
Figure 8:
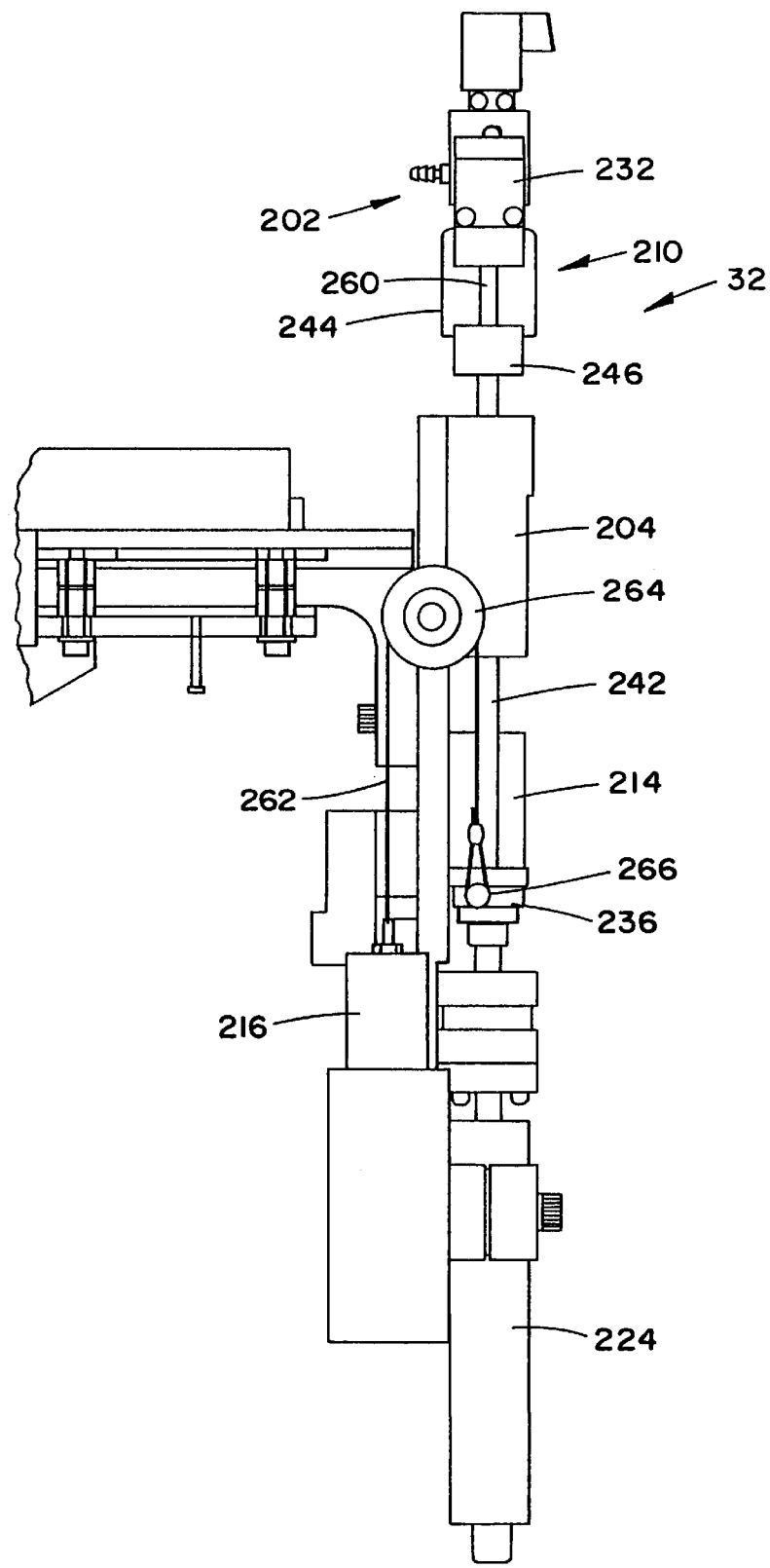

As mentioned above, after packaging mechanism 16 completes a work cycle, usually rotary dial 36 is indexed one step. FIG. 6 is a flow chart outlining this indexing procedure 100. At step 102, the control system 20 will determine whether rotary dial 22 of swaging mechanism 14 has been indexed the number of times needed to place the appropriate number of needles in the package on dial 36 at work station 34. Once that needed number of moves by dial 22 has taken place, a done bit is set at step 104.

A check is made at step 106 to determine whether all the stations 42, 44, 34, 46, 50, 52, 54 and 56 of packaging mechanism 14 have completed their respective operations, and in particular, whether the mechanisms at these stations have returned to home positions. If one of these mechanisms has not returned to its home position, then, at step 110, the machine 10 is stopped and a cycle jam routine is started. However, if at step 106, all of the mechanisms of the packaging work stations have returned to their home positions, the routine 100 proceeds to step 112, and the packaging dial 36 is indexed one position, inter alia, to move a new, empty package to station 34.

Figure 5:
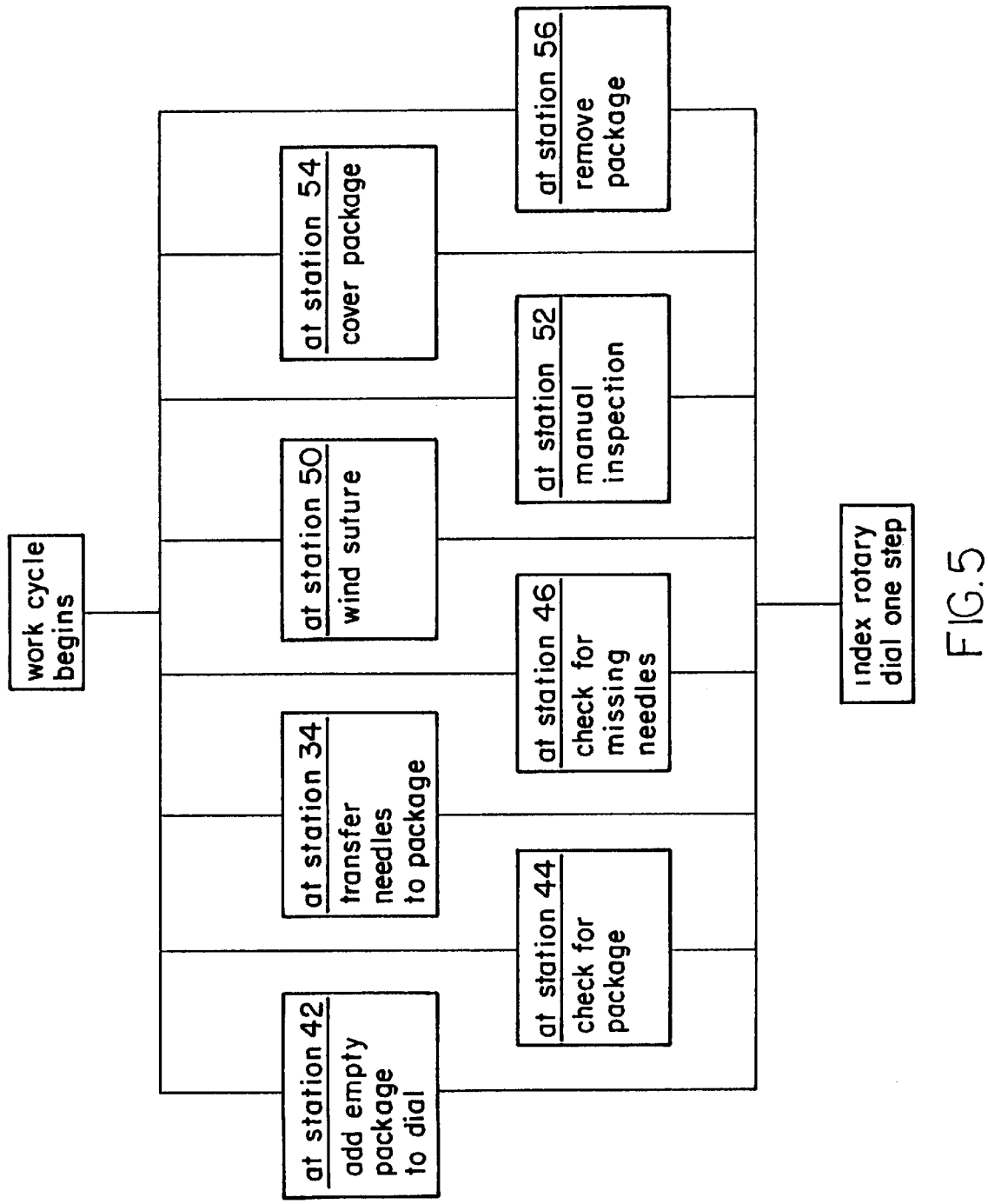
FIG. 5 is a flow chart illustrating the general operation of a packaging mechanism of the machine.

A check is made at step 114 to verify whether the packaging dial has stopped indexing. If that dial has not stopped moving, then the system will perform a check at step 116 to determine whether a predetermined time period has expired. If this time period has expired, a time-out flag has been generated by the control system indicating a condition referred to as a time-out error. If this is the case at step 116, the process will be terminated and prompted for re-initialization at step 120. In contrast, if a time-out flag has not been generated at step 116, the check is made again to determine if the packaging dial 36 has finished rotating, or indexing, for approximately 45 to the next successive workstation. If the packaging dial finishes indexing before the time-out flag is generated, then the done bit that had been set at step 104 is cleared at step 122 and the work cycle of FIG. 5 is repeated.

FIGS. 7 through 27 illustrate in greater detail various specific workstations of machine 10 and various routines or procedures that are performed at those workstations.

The Pull Test Station

For example, FIGS. 7–11 show pull test station 32. This station is used to perform two types of pull tests, referred to as non-destructive and destructive pull tests, and discussed in greater detail below. Generally, in the non-destructive pull test, a suture that has been swaged to a needle is gripped and pulled. The needle passes the test if the suture does not break, and the needle fails the test if the suture breaks. In the destructive pull test, a suture is gripped, pulled and normally broken away from the needle, and the general purpose of this test is to help prevent the swaging station 30 from swaging the sutures too tightly to the needles.

One of these two test is given to each needle brought to the pull test station 32. The specific proportion of the needles that are given each test may vary, however, Preferably, though, the vast majority of the needles are given the non-destructive pull test; and for example, forty-nine out of fifty needles may be given the non-destructive test, and one of every fifty needles may be given the destructive pull test.

Pull test station 32 includes suture gripping assembly 202, stationary guide block 204, lower slide block assembly 206, load cell assembly 210, and air cylinders 212 and 214. Preferably station 32 further includes counterweight 216, proximity switches 220 and 222, speed controller 224, and processing logic unit 226. More specifically, gripping assembly 202 includes gripper arms 230 and 232 and gripper actuator 234; and lower slide block assembly 206 includes lower slide block 236 and slide rods 240 and 242. Load cell assembly 210 includes load cell 244, plates 246 and 250, guide rods 252 and 254 and separating springs 256 and 260, and preferably load cell 244 is a piezo electric transducer.

Generally, in the operation of pull test station 32, multi-axis grippers 24 on rotary disc 22 carry sutured needles, one at a time, to the pull test station. At that station, gripping assembly 202 is employed to grip the needle sutures; and slide block assembly 206, air cylinders 212 and 214 and counterweight 216 are used to apply controlled pulling forces on grippers 230 and 232 and, thereby, to apply controlled pulling forces on the needles sutures. Load cell assembly 210, and specifically, load cell 244, is used to measure those pulling forces, and these force measurements are transmitted to the system computer by conventional means. Also, proximity sensors 220 and 222 are used to identify when lower slide block 236 reaches various positions, and speed controller 224 may be provided to help control the speed of the lower slide block. Processing logic unit 226 may be used to implement and to operate the pull tests conducted at the pull test station, and to process related data.

With the embodiment of pull test station 32 shown in FIGS. 7–11, load cell assembly 210 is slidably mounted on and extends upwards from stationary guide block 204. In particular, guide rods 252 and 254 are supported by and extend upward from guide block 204, and these guide rods are connected to and support plate 246. Plate 250 is substantially parallel to and is spaced above plate 246. Separating springs 256 and 260 are connected to and extend between plates 246 and 250, and load cell is securely captured between those plates. Springs 256 and 260 are tension springs and tend to pull plates 246 and 250 together, so that the plates hold load cell 244 between the plates.

Gripper assembly 202 is supported by and is located above load cell assembly 210, and the gripper assembly supports gripper arms 230 and 232 for movement between open and closed positions. In the open position, the gripper arms are spaced from and do not engage the needle suture; and in the closed position of the gripper arms, the needle suture is tightly clamped between those arms. Preferably, in the closed, or gripping, position, arms 230 and 232 grip the suture slightly below the needle 64. Gripper actuator 234 is provided to move gripper arms 230 and 232 between their open and closed positions.

Figure 9:
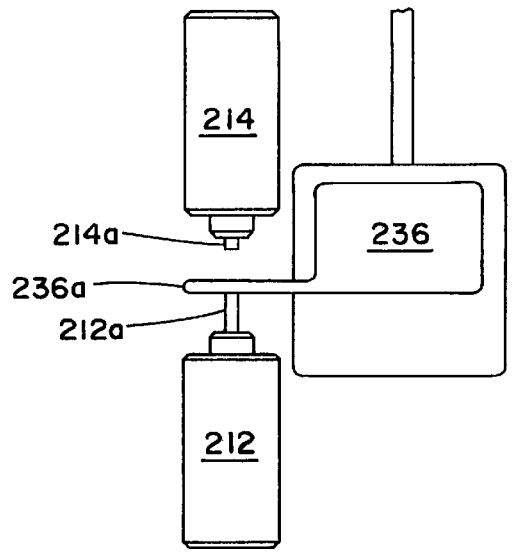
FIG. 9 is a top view of a needle mounting assembly of the pull test station.
Figure 10:
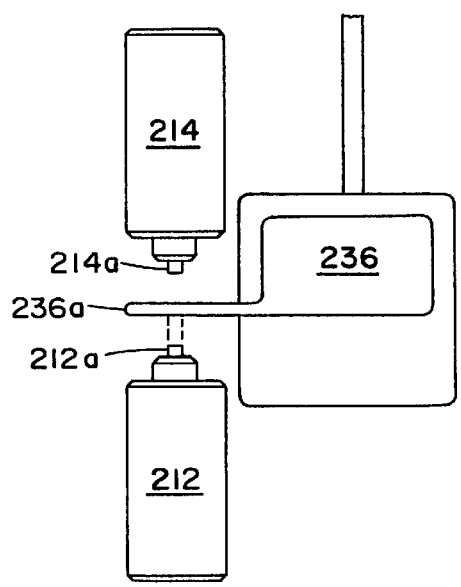
FIGS. 10 ante 11 illustrate a slide assembly of the pull test station.
Figure 11:
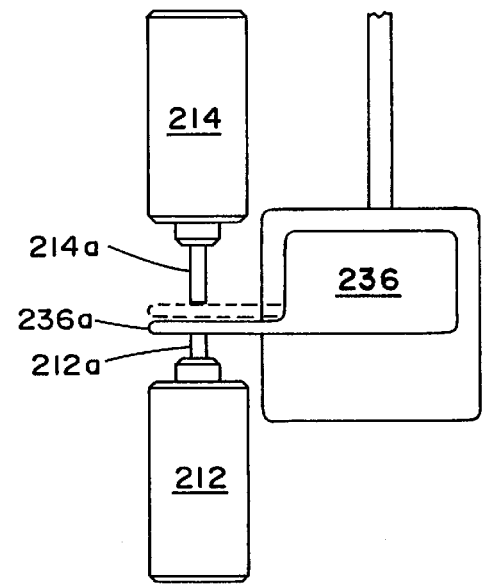

With particular reference to FIGS. 9–11, slide rods 240 and 242 extend downward from stationary guide block 204 and are connected to lower slide block 236, which includes projection or finger 236a. Air cylinders 212 and 214 include piston rods 212a and 214a, and these piston rods are positioned and operated to act on finger 236a. In particular, piston rods 212a and 214a are operated to apply upward and downward forces, respectively, on finger 232a. As shown in FIG. 9, piston rod 212a is in an extended position, and provides an upward force that supports finger 232a and slide block 232 at a fixed vertical position. In addition, slide block 232 is counterweighted to a net downward weight of two to five ounces by counterweight 216, which acts on the slide block through cable 262, around pulley 264 and through attachment point 266.

To perform the non-destructive pull test, piston rod 212a of cylinder 212 is retracted from the position shown in FIG. 9 to the position shown in solid lines in FIG. 10. This removes the upward supporting force that piston rod 212a had applied to finger 236a; and as a result, the counterbalanced net downward weight of slide block 236 is applied to finger 236a and—via that finger, slide block 236 and gripper arms 230 and 232—to the needle suture.

To perform the destructive pull test, piston rod 212a is retracted and piston rod 214a is extended from the position shown in FIG. 9 to the position shown in FIG. 11. This results in the vertical displacement of finger 236a from the position shown in FIG. 9 to the position shown in FIG. 11. This produces a downward force on slide block 236, which, through slide rods 240 and 242, moves grippers 230 and 232 downward, causing a downward pulling force on the needle suture.

The Non-Destructive Pull Test

Figure 12:
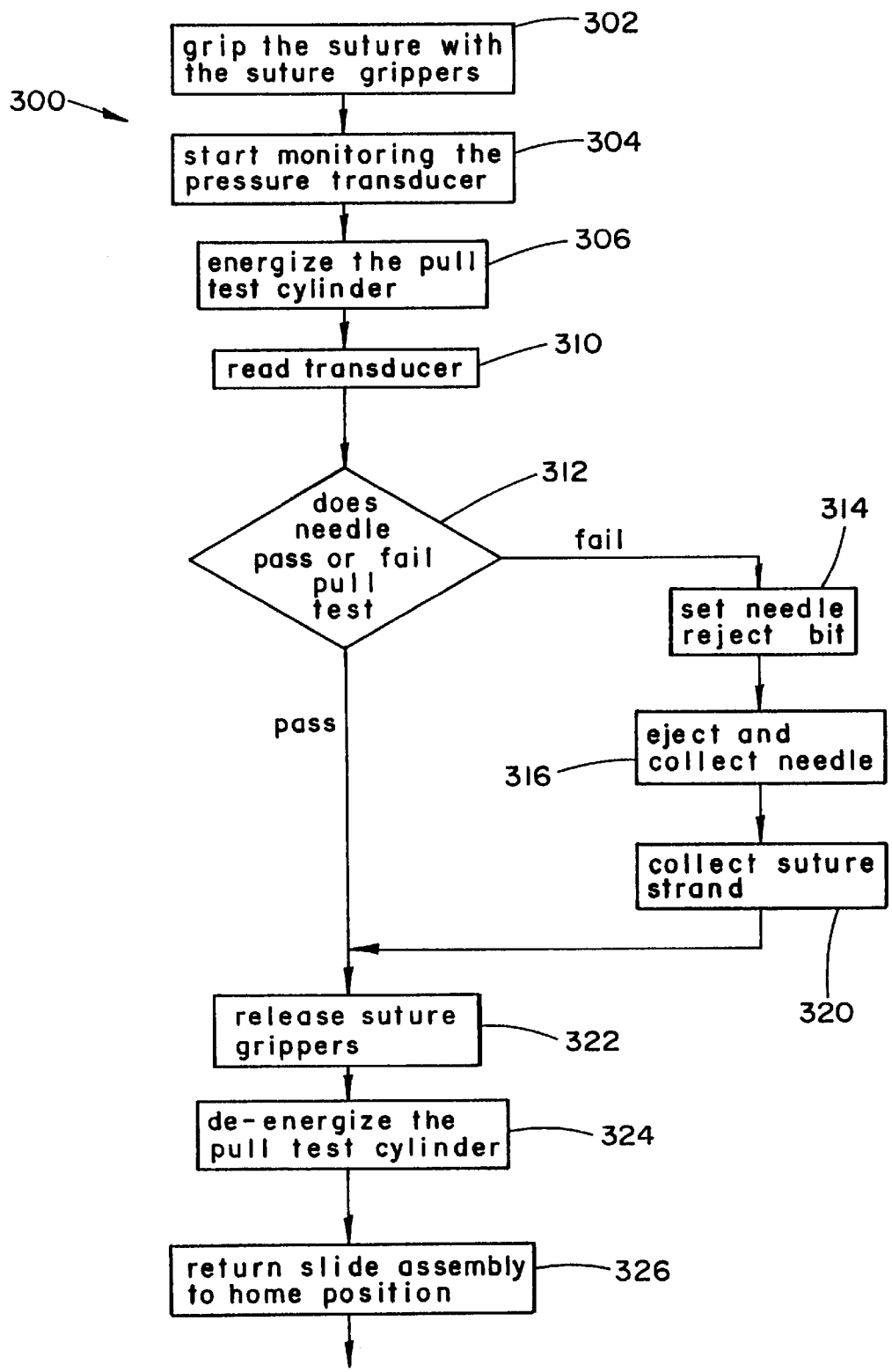
FIGS. 12 and 13 are flow charts showing a test, referred to as a non-destructive pull test, performed at the pull test station.
Figure 13:
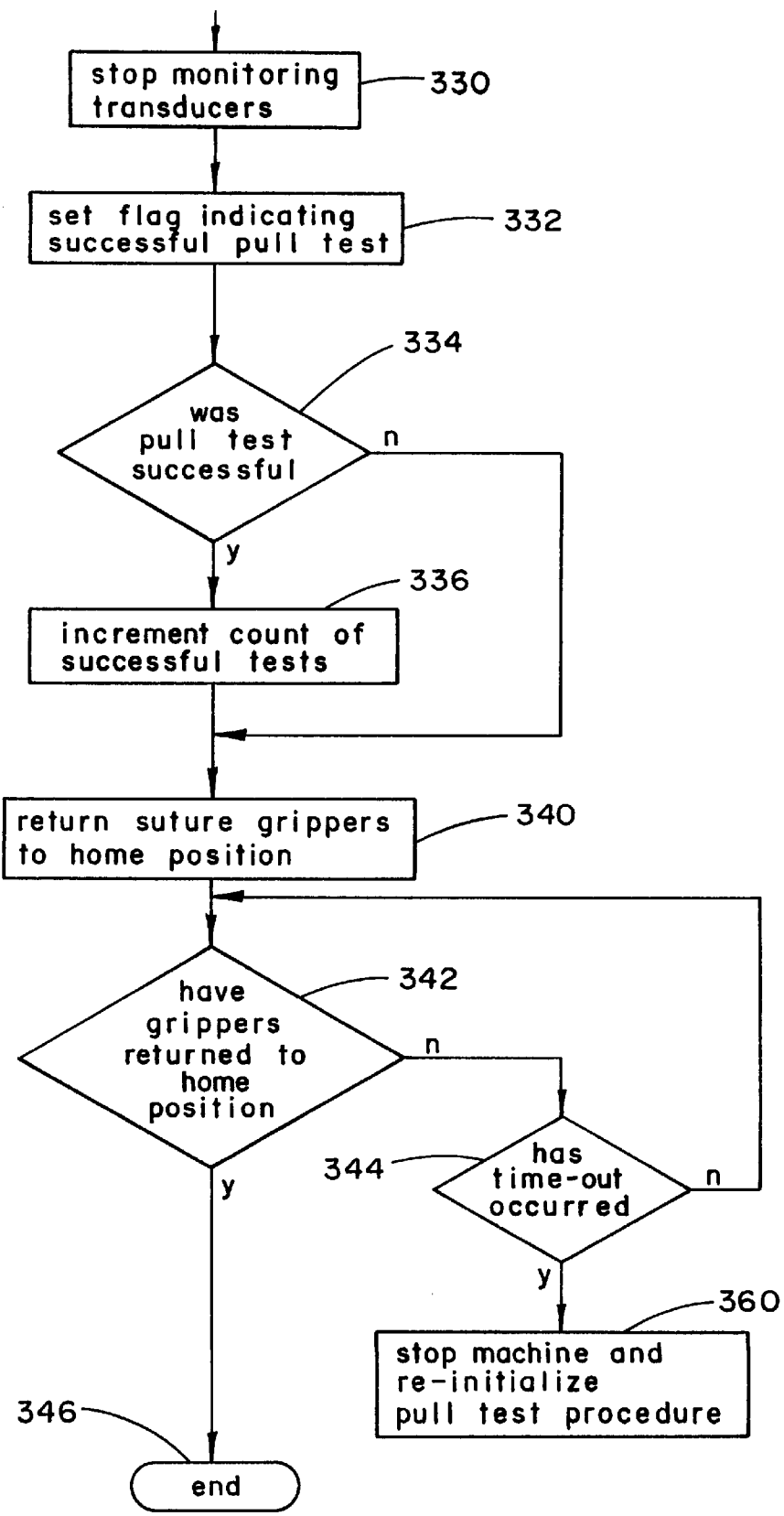

The complete non-destructive pull test is shown in the flow charts of FIGS. 12 and 13. In this test, as mentioned above, a suture that has been swaged to a needle is gripped and pulled; and the needle passes the test if the suture does not break, and the needle fails the test if the suture breaks.

In accordance with this routine 300, after a needle is positioned at pull test station 32, then at step 302 gripper arms 230 and 232 are moved from the open or retracted position to the closed position to grip the suture strand slightly below the needle 64. Next, at step 304, processor begins to monitor the pressure applied to the load cell; and at step 306, cylinder 212 is operated to retract piston rod 212a so that slide assembly 206 pulls grippers 230 and 232 downward, thereby applying a force on the needle suture and on transducer 244.

Cylinder 212 may be energized for a relatively short period of time, preferably ranging in milliseconds; and during this time, processor 226 continues to monitor or read the pressure applied to transducer 244, as represented by step 310, and the processor determines whether the needle passes or fails the pull test, as represented by step 312. Any suitable specific procedure or subroutine may be used to make this determination. For example, typically, the pressure on transducer 216 will rise to a given level and then, as long as the suture does not break away from the needle, the pressure will stay at that level for the remainder of the pull test. Processor may determine that the needle passes or fails the pull test if, after a predetermined length of time, the pressure on transducer 244 is, respectively, above or below a preset value.

If the needle fails the pull test, the routine proceeds through steps 314, 316 and 320, where the needle reject bit or flag is set in processor, the needle is ejected from gripper 24 and collected, and the suture strand is also collected. From step 320, routine 300 then proceeds to step 322. If, at step 312, the needle passes the pull test, then the routine proceeds directly to step 322 and skips steps 312, 316 and 320. At step 322, gripper arms 230 and 232 are released from their grip on the suture strand. Then, at steps 324 and 326, the pull test cylinder 212 is de-energized, and the slide assembly 206 is moved to a home position.

Next, at steps 330 and 332, the processor stops monitoring transducer 244, and the processor sets a bit or flag indicating that the pull test is completed. From step 332, routine 300 proceeds to step 334, where the processor determines whether the pull test was successful—that is, whether the needle passed the test. If the needle passed the test, a count of successful tests is increased by one at step 336, and the routine moves on to step 340. If the needle did not pass the test, step 336 is skipped, and the routine proceeds from step 334 directly to step 340.

At step 340, suture grippers 230 and 232 are moved to a home position; and then, at step 342, the processor checks to determine whether grippers 230 and 232 have reached their home position. If the gripper arms have not reached that position, the processor will repeat this check until either the grippers reach that position or a predetermined length of time has expired. More specifically, if at step 342, the gripper arms have not reached the home position, the routine proceeds to step 344, where the processor determines whether the predetermined length of time has expired, or timed out. If that length of time has not expired, the routine returns to step 342, and steps 342 and 344 are repeated until, as mentioned above, either the suture grippers return to the home position or the predetermined length of time expires. In the former case, the routine ends, as indicated at step 346; and in the latter case, processor stops the machine and re-initializes the pull test procedure, as indicated at step 350.

Destructive Pull Test

Figure 14:
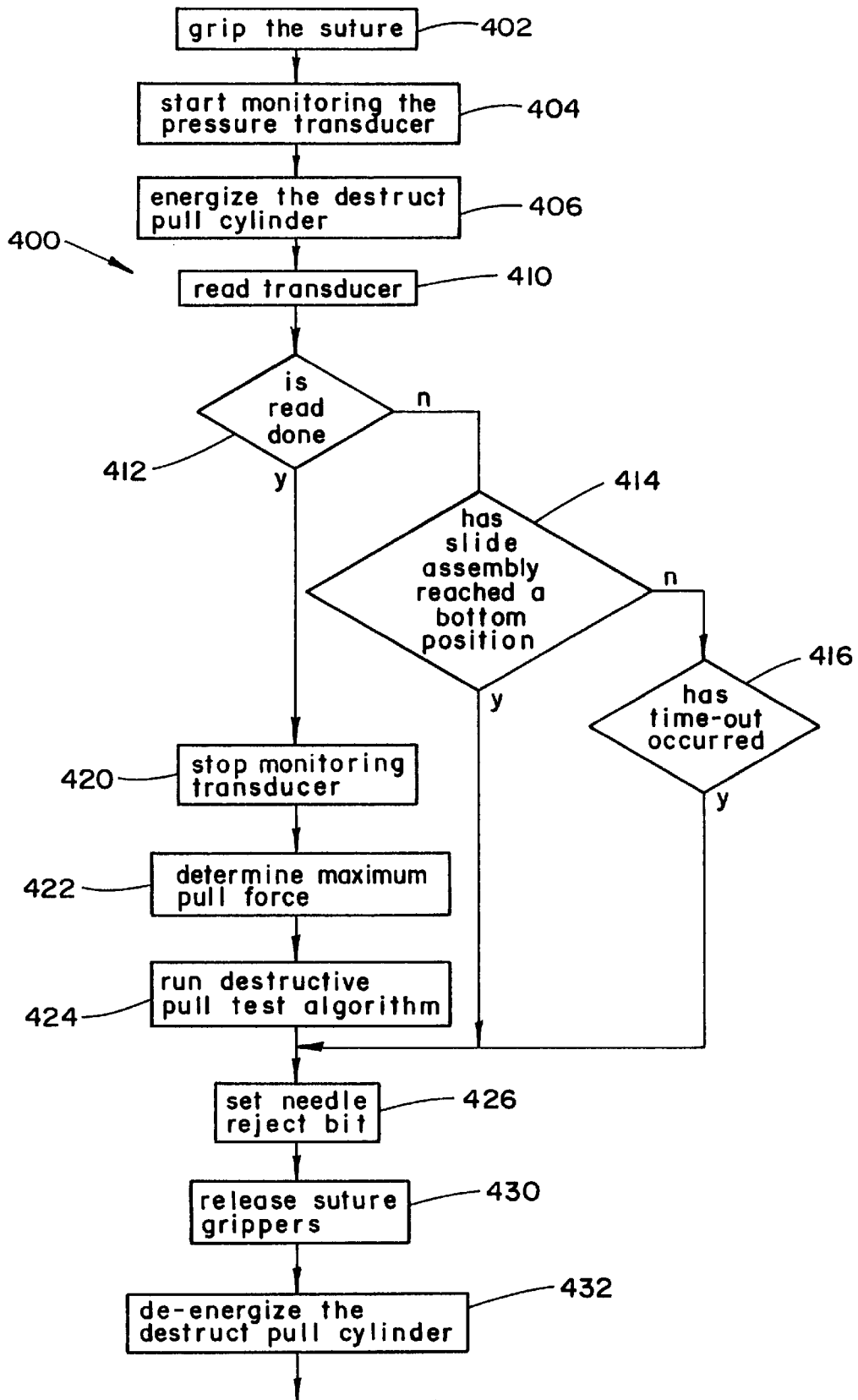
FIGS. 14 and 15 are flow charts illustrating a second test, referred to as a destructive pull test, also performed at the pull test station.
Figure 15:
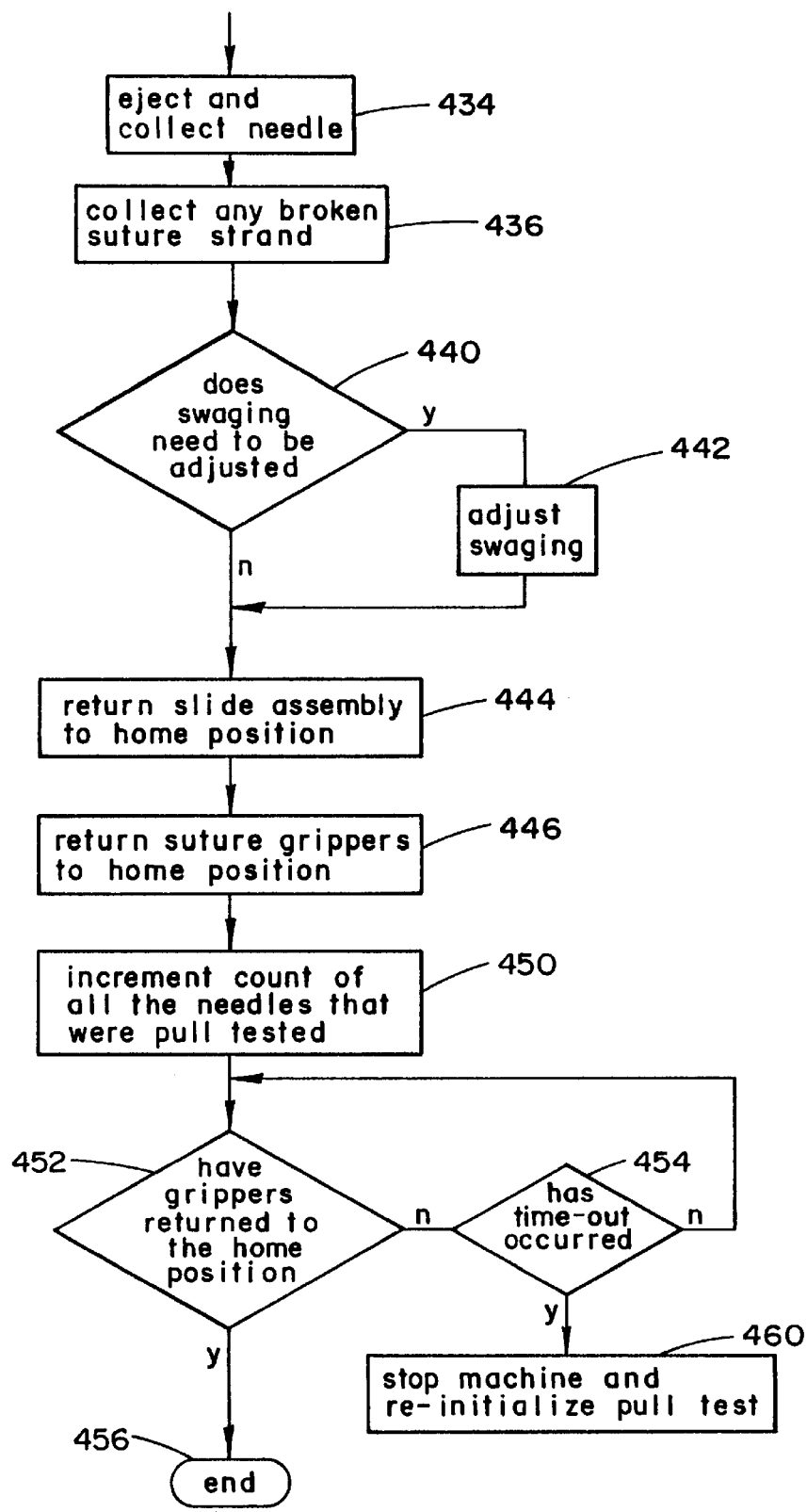

FIGS. 14 and 15 show a flow chart of the destructive pull test. As previously mentioned, in this test, a suture is gripped, pulled, and normally broken away from the needle, and the general purpose of the test is to help prevent the sutures from being swaged too tightly to the needles at swaging station 30.

More specifically, the destructive pull test is used to help set swage dies at the swaging station, and to help prevent the swaging pressure from becoming too high. The destructive pull test is very similar to the non-destructive pull test. Two important differences between the two tests, however, are that in the destructive test, first, piston 214a of cylinder 214 is extended to force slide block 236 and grippers 230 and 232 downward, and second, the pressure or force applied to the suture is, normally, sufficient to break the suture strand away from the needle.

In accordance with this procedure 400, after a needle is positioned at pull test station 32, then at step 402, suture grippers 230 and 232 are extended to grip the suture strand slightly below the needle 64. Next, at step 404, processor 226 begins to monitor the pressure applied to transducer 244; and, at step 406, cylinder 214 is energized to extend piston rod 214a and to push slide assembly 206 and grippers 230 and 232 downward, thereby applying a force on the suture and on transducer 244. For example, piston rod 214a may be designed to provide a fixed length stroke against slide finger 236a, and this results in the vertical displacement of the slide finger from the position shown in FIG. 9, to the position shown in solid lines in FIG. 11.

At step 410, the processor begins to read, or measure, the pressure applied to transducer 244. Preferably, these measurements are made, or read, a number of times, such as 100 times, and these readings are all stored in the processor memory. As these readings are taken, the processor repeatedly checks to determine if the required number of readings have been taken, as represented by step 412.

If, at step 412, the required number of readings has not been taken, the routine moves to step 414, where the processor checks for a signal from sensor 222 indicating that the slide assembly 206 has reached a predetermined bottom position, a result referred to as bottoming out. If the slide assembly has not bottomed out at step 412, the processor then determines, at step 416, whether a predetermined length of time has expired, or timed out. If that length of time has not expired, routine 400 returns to step 412 and steps 412, 414 and 416 are repeated until the predetermined number of transducer readings have been taken, the slide assembly has bottomed out, or the predetermined length of time has expired.

If at step 412, the predetermined number of readings have been taken, the processor proceeds to step 420 and 422, where the processor stops monitoring the transducer 244, and a maximum pull force is determined. Any suitable specific procedure or subroutine may be used to determine this maximum pull force. For instance, typically, during the destructive pull test, the pressure on the transducer 244 will gradually rise and then suddenly drop when the suture breaks; and the processor may be programmed to calculate the maximum pull force as the average of a given number, such as ten, of these pressure readings prior to the sudden decrease in the pull force. In the event the suture does not break during the destructive pull test, the pressure on transducer 244 may gradually rise over the whole period of the pull test, and the processor may calculate the maximum pull force as the average of a given number of pressure readings immediately prior to the end of the pull test.

After the maximum pull force has been measured or calculated, processor performs a subroutine 424, referred to as a destructive pull test algorithm, which may be used for a number of purposes. For instance, this algorithm may be used to change the frequency at which the destructive pull test is given. Also, the algorithm may be used to determine whether the swaging pressure should be increased or decreased. One suitable pull test algorithm is disclosed in copending patent application Ser. No. 08/804,475 now U.S. Pat. No. 5,920,482.

From step 424, routine 400 proceeds to step 426, where the needle reject bit is set. The routine may also proceed to step 426 directly from steps 414 and 416, skipping steps 420, 422 and 424. More specifically, the routine proceeds to step 426 directly from step 414 if at this latter step, slide assembly 206 has bottomed out; and the routine proceeds directly to step 426 from step 416 if at the latter step, the predetermined length of time has expired.

After step 426, the procedure 400 proceeds through steps 430 and 432, where the suture grippers 230 and 232 are released from their grip on the suture, and the destruct pull cylinder 214 is de-energized. At step 434, the needle is ejected from the needle gripper 24 at pull test station 32 and collected, and at step 436, any broken suture strand is collected.

After step 436, routine 400 proceeds to step 440, where the processor determines whether any changes are to be made to the swaging process. If changes are to be made, then those changes are made at step 442 and the routine moves on to step 444. If at step 440, it is determined that no changes are to be made to the swaging process, the routine 400 proceeds directly to step 444, skipping step 442. At step 444, the slide assembly is returned to its home position, and sensor 220 may be used to indicate that this has occurred. The suture grippers 230 and 232 are returned to their home position at step 446, and a count of all the needles that were pull tested is increased by one at step 450.

Then, at step 452, the processor checks to determine whether grippers 230 and 232 have reached their home position. If the suture grippers have not reached that position, the processor will repeat this check until either the grippers reach that position or a predetermined length of time has expired, as represented by step 454. If the grippers reach their home position before the timer times out, the routine ends at step 456. However, if the timer times out before the grippers reach their home position, the processor stops machine 10 and re-initializes the pull test procedure, as represented by step 460.

The Needle-To-Package Transfer Station

Figure 16:
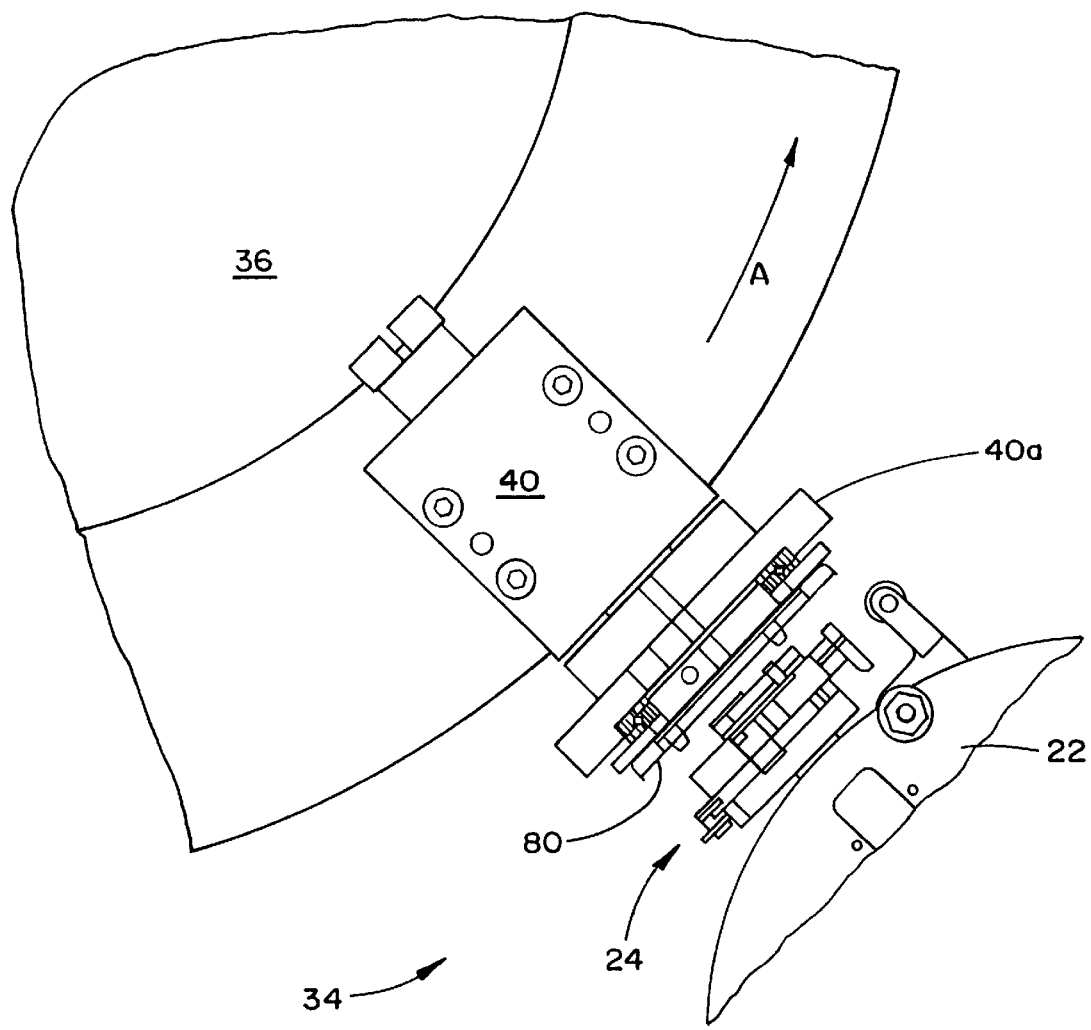
FIG. 16 is a top view of a needle-to-package transfer station of the machine of FIG. 1.
Figure 17:
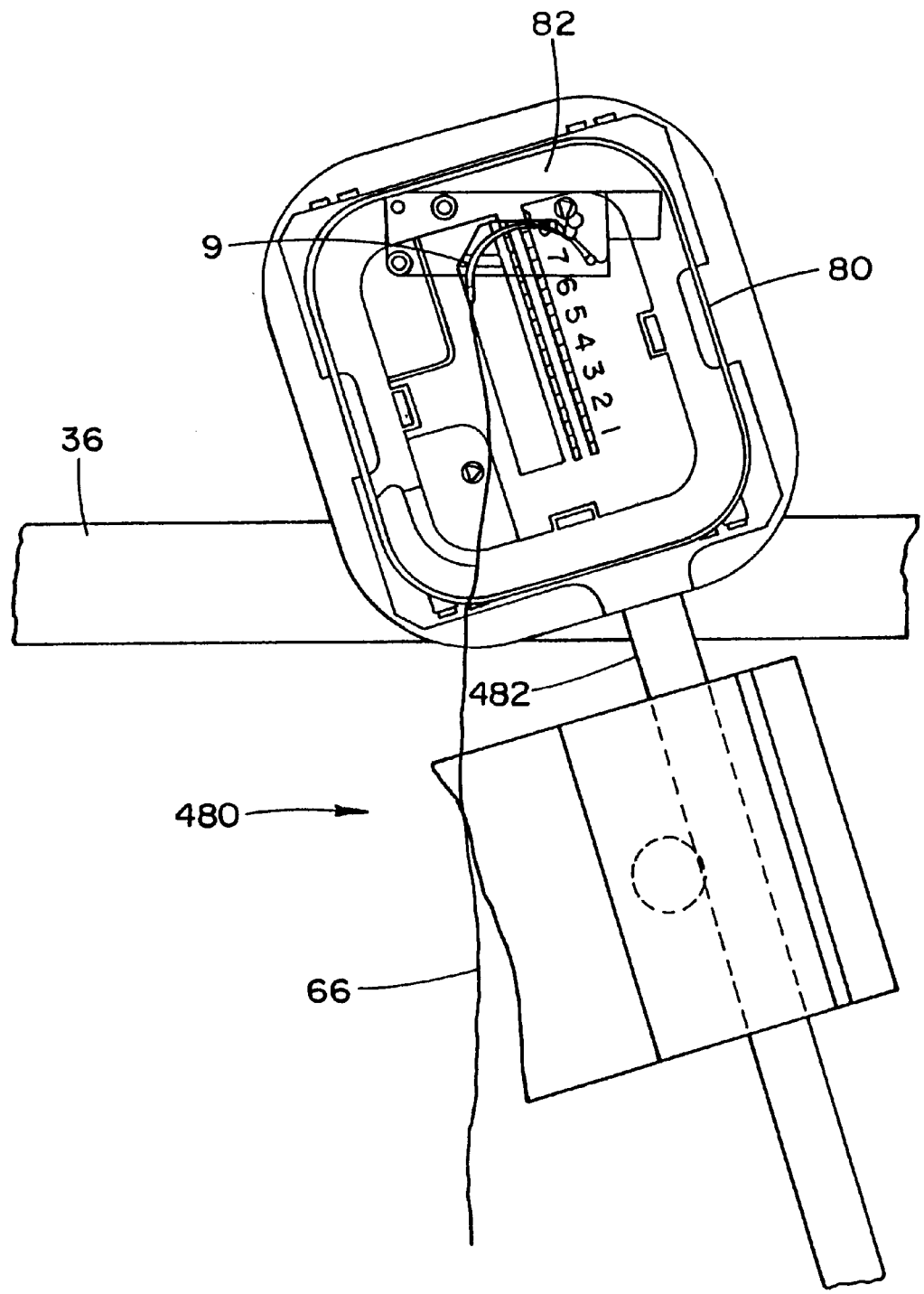
FIG. 17 shows a tool nest and package tray at the needle-to-package transfer station.
Figure 18:
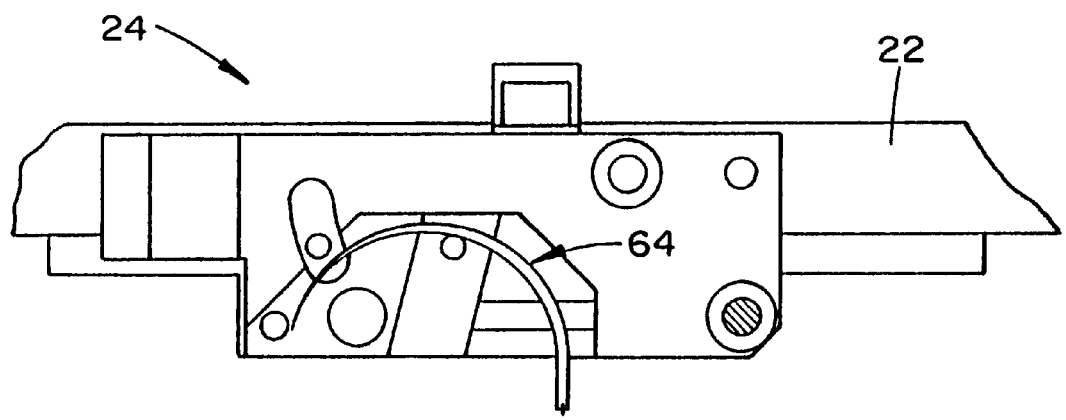
FIG. 18 shows a needle gripper at the needle-to-package transfer station.

FIGS. 16–18 illustrate station 34 in greater detail. Generally, at this station, a package tray 80 mounted on one of the tool nests 40 of mechanism 16 faces one of the grippers 24 of mechanism 14. This work station 34 also includes a tilting assembly (not shown) and an elevator assembly 480 including an elevator shaft 482 and an elevator motor (not shown). A processing logic unit may be provided at work station 34 to implement and to operate the procedures employed at the station and to process related data.

Generally, at station 34, the above-mentioned tilting mechanism is used to tilt the tool nest 40 from a substantially vertical orientation to a tilted orientation, as shown in FIG. 17. This tilt may be between 10–20 degrees, and most preferably about 16 degrees, from the vertical. As a result of this tilting, the needles placed in tray 80 are laterally slightly shifted relative to each other so that the sutures extending downward from the needles will not tend to become tangled with each other. Elevator assembly 480 is used to raise tool nest 40 and package tray 80 through a series of small discrete steps so that the needles transferred into the package tray are vertically slightly offset with respect to each other.

The Needle-Package Transfer Procedure

Figure 19:
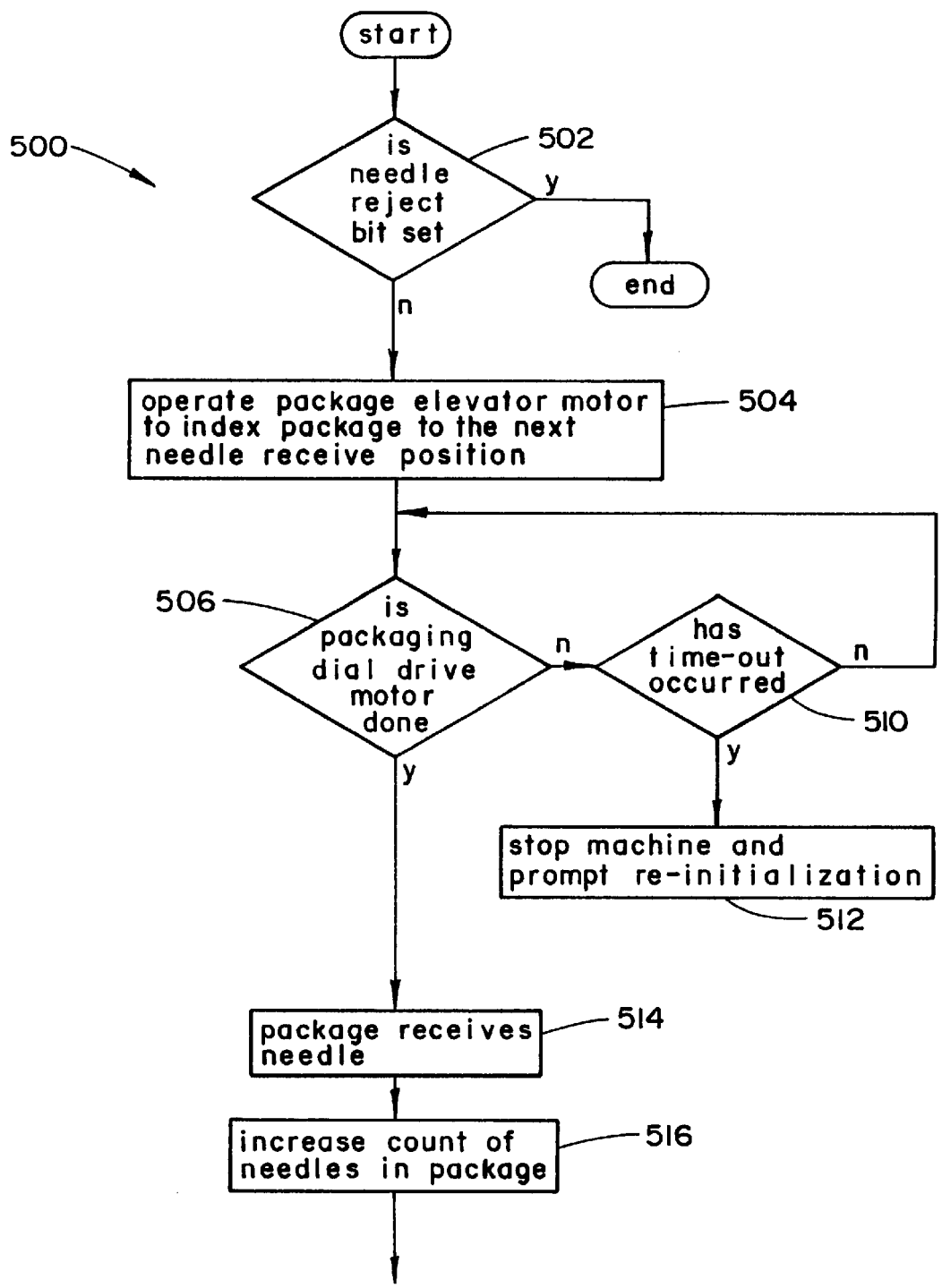
FIGS. 19, 20 and 21 show a procedure for operating the needle-to-package transfer station.
Figure 20:
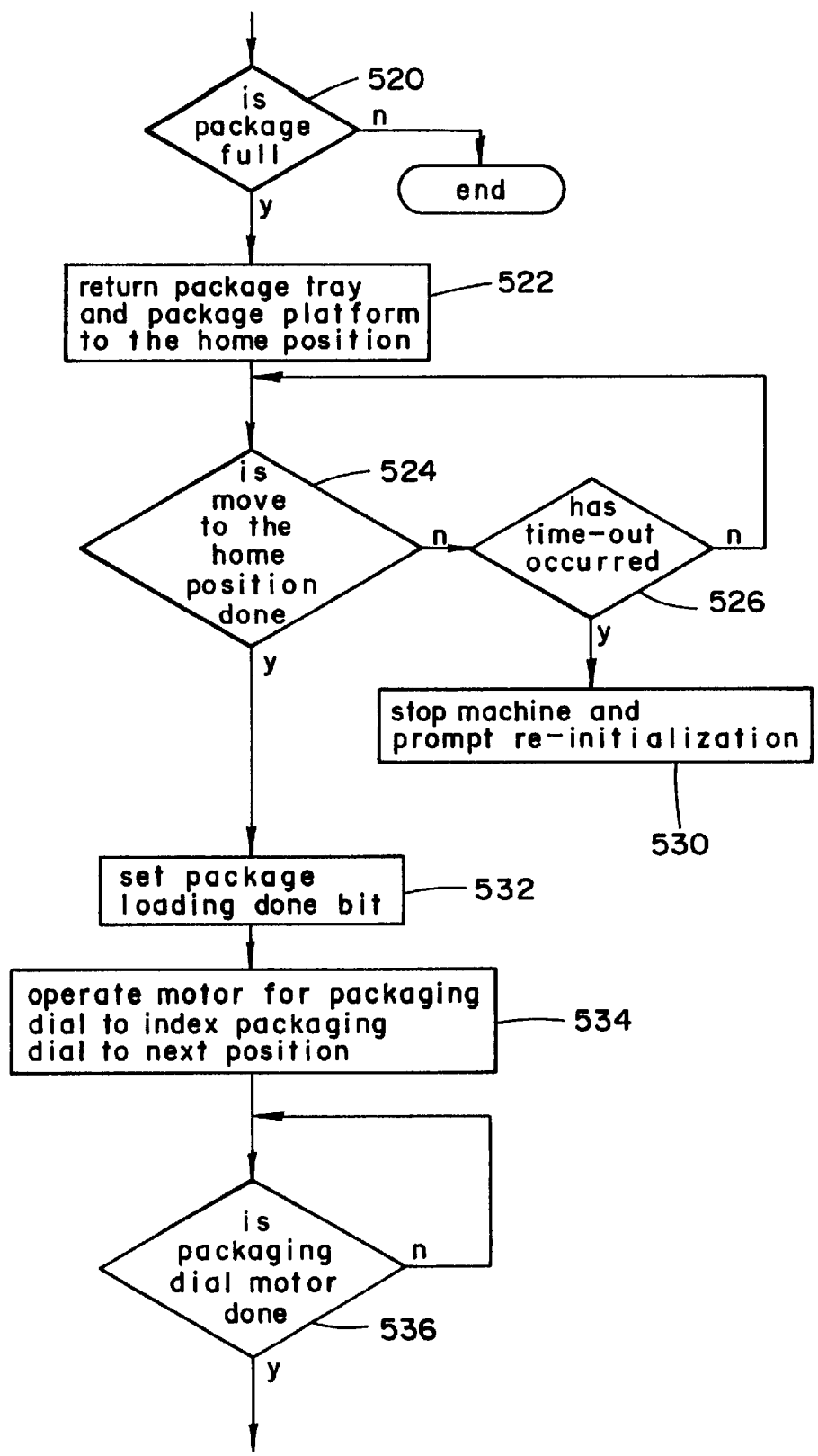
Figure 21:
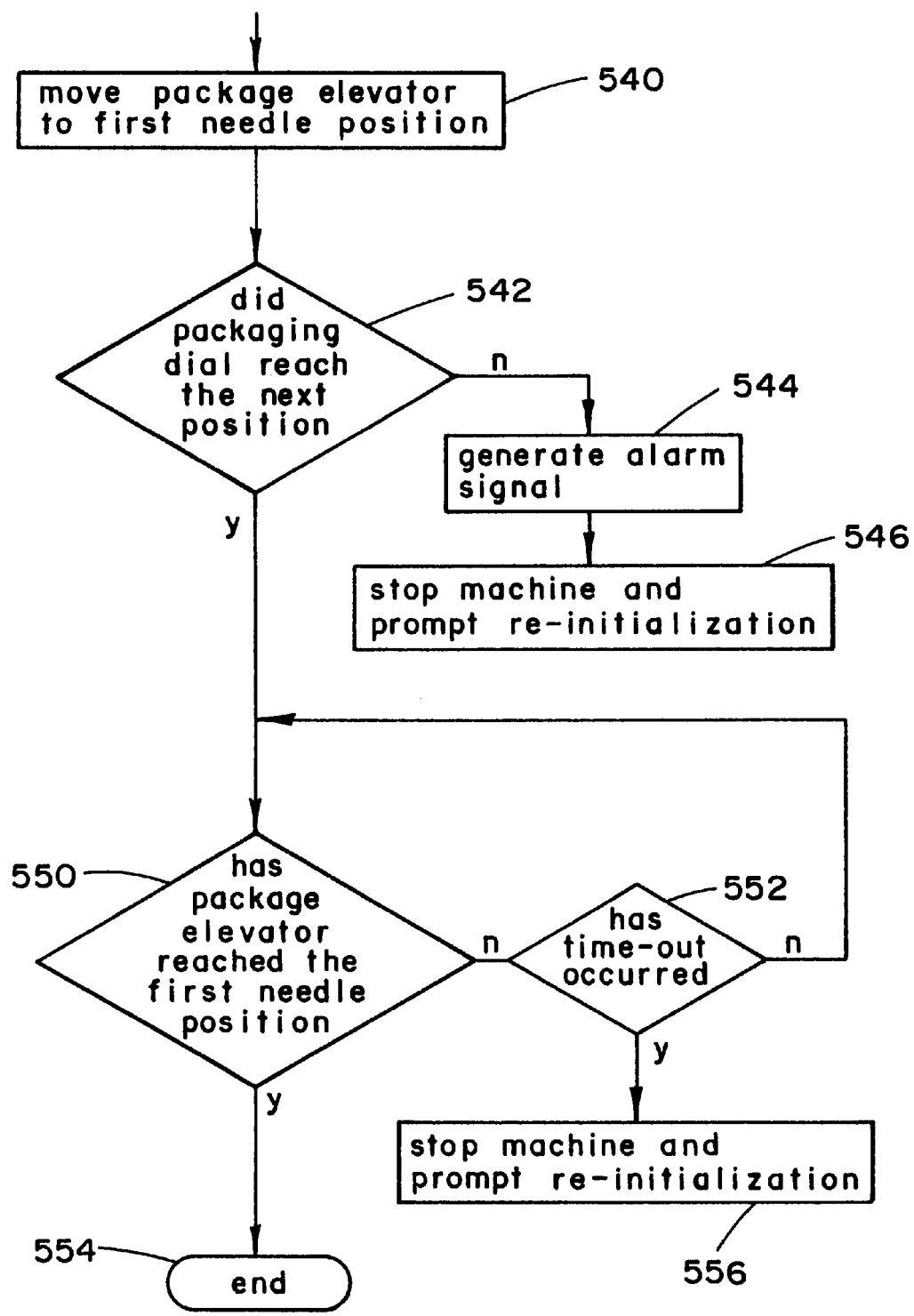

FIGS. 19, 20 and 21 illustrate a specific procedure for operating station 34. Generally, this procedure 500 is started when an empty package tray 80 on dial 36 and an armed needle on dial 22 are moved to work station 34. Once the procedure is begun, then, at step 502, a check is made to determine if the needle reject bit is set at station 34. If this bit is set, an armed needle is not at this work station. Procedure 500 then terminates, and station 34 remains in a hold position until the next multi-axis gripper 24 on dial 22 is moved to this station.

If, however, the needle reject bit is not set, then procedure 500 moves on to step 504 At this step, if the needle package 80 is not in the first needle receiving position, then the elevator shaft motor is operated to move the needle package to the next needle receive position. In contrast, if at step 504, the needle package 80 is in the first needle receive position, then it is not necessary to move the package, and the routine skips step 504.

In procedure 500, the status of a motor used to drive dial 36 is continuously monitored, as represented by step 506, to insure that the package tray 80 at work station 34 is properly indexed. Until that motor is done, the control system will perform a check at step 510 to determine whether a time-out flag has been generated by the control system that would indicate a time-out error. If the time-out flag has not been generated, the monitoring at step 506 continues. However, if the time-out flag has been generated, the process will terminate and the control system will prompt re-initialization of machine 10 at step 512.

If the packaging dial motor has properly indexed the packaging dial 36, then, at step 514, the armed needle on the gripper 24 at station 34 is inserted into package tray 80; and, at step 516, a count of the needles in the package at station 34 is increased by one. Then, at step 520, this count is compared to the number of needles that package is supposed to receive. The preferred embodiment of package tray 80 shown in FIGS. 3 and 4 is designed to receive eight needles. As will be understood by those of ordinary skill in the art, the present invention may be used with packages that receive more or fewer needles.

If the test done at step 520 shows that package 80 is not filled, then routine 500 ends, and work station 34 awaits for the arrival of the next needle on mechanism 14. If, though, at step 520, packge 80 is filled, routine 500 proceeds to step 524, where the package platform and the needle package are returned to a home position at station 34 in preparation for movement to station 46. A continuous check is made, as represented by step 524, to determine whether package tray 80 has been returned to its home positon.

Until the package tray has been indexed back to its home position, the control system will perform a check at step 526 to determine whether a time-out flag has been generated by the control system, indicating a time out error. If the time-out flag has been generated, the process will be terminated and the control processor will prompt re-initialization of machine 10, as represented by step 530.

If, though, package tray 80 returns to its home position before the time-out flag is generated, then the package is fully loaded with needles and is ready for further processing at subsequent stations around the packaging dial 36. To indicate this condition, a done bit is set at step 532.

Once this bit is set, then at step 534, the motor for the packaging dial 36 is operated to move, or index, the packaging dial one step. The processor checks, at step 536, to determine whether the packaging dial motor is done indexing the packaging dial. Once this motor is done, the motor for the package elevator 482 is operated at step 540 to return that elevator to the first needle position—that is, the position in which the elevator holds a package 80 at the location where the package receives its first needle.

After step 540, the processor checks, at step 542, to determine whether the packaging dial has been indexed to the next position. If the packaging dial has not been properly indexed, an alarm signal is generated at step 544 and, at step 546, machine 10 is halted and the processor prompts re-initialization of the machine.

If, at step 542, the packaging dial 36 is at the next position, then, at step 550, the processor monitors to determine whether the package elevator 482 has reached the first needle position; and this monitoring is continued until either a predetermined length of time expires, or that package elevator reaches that home position. More specifically, if, at step 550, the elevator 482 is not at the home position, routine 500 proceeds to step 552, where the processor checks to determine if that predetermined length of time has expired. If that length of time has not expired, then the routine returns to step 550. Steps 550 and 552 are repeated until either the package elevator 482 reaches the home position, or the predetermined length of time expires. In the former case, routine 500 ends at step 554; while in the latter case, the control system 22 stops machine 10 and prompts re-initialization, as represented by step 556

Hanging Suture Detection Procedure

Figure 22:
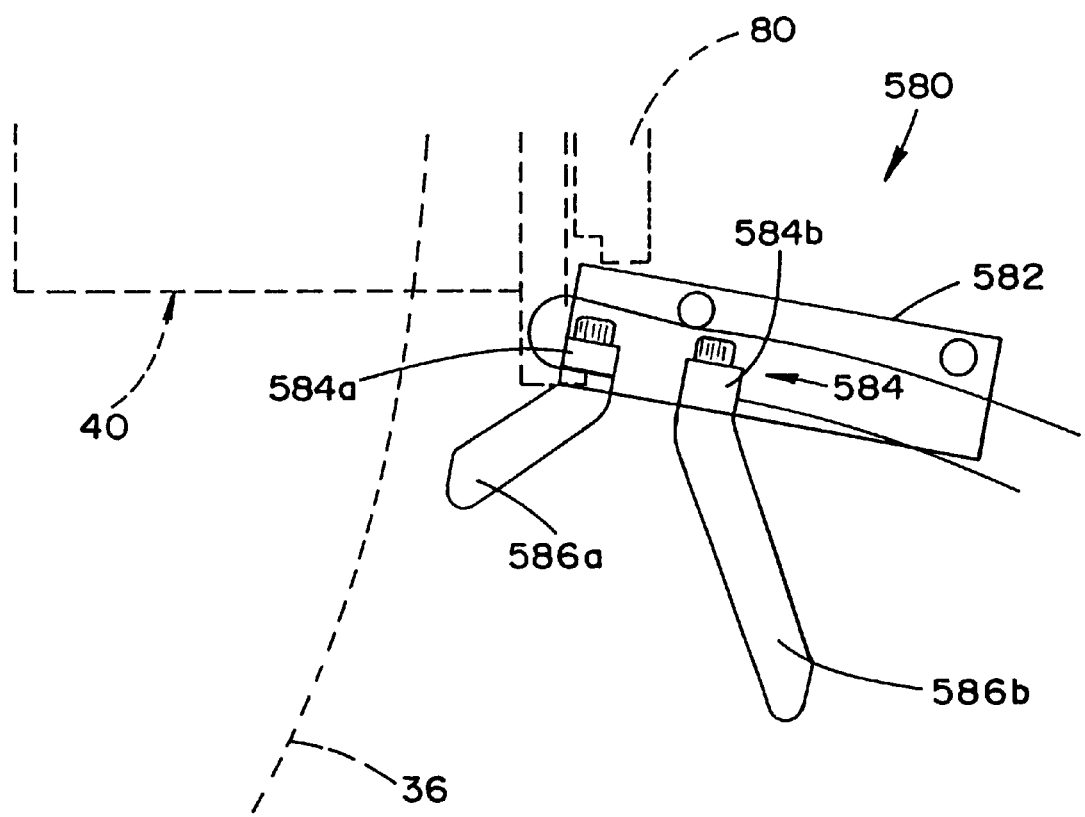
FIG. 22 shows a hanging suture detector that may be used in the machine of FIG. 1.
Figure 23:
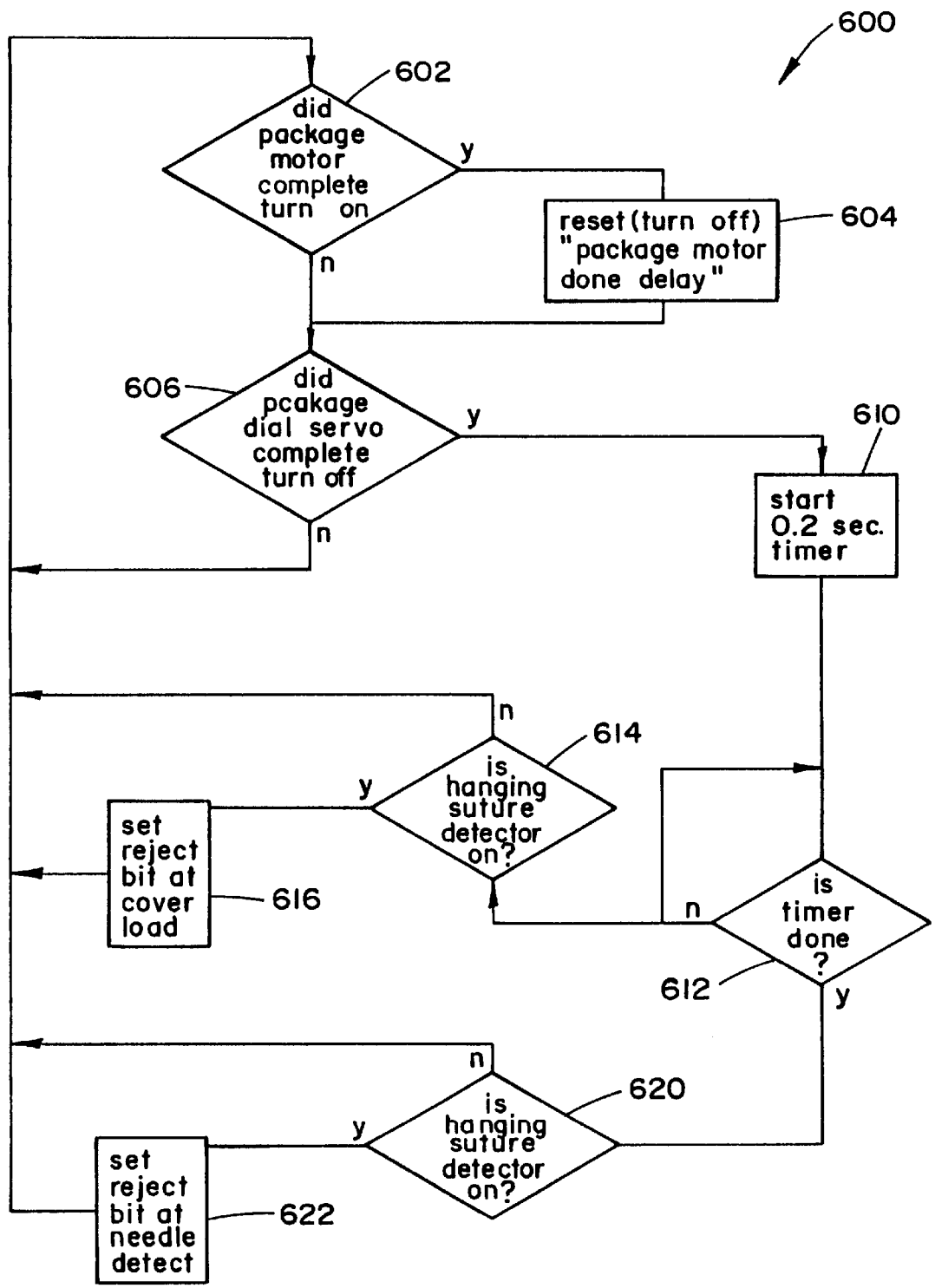
FIG. 23 is a flow chart illustrating a routine for detecting hanging sutures on needle packages.

FIGS. 22 and 23 illustrate a detector unit and a procedure, respectively, for detecting a hanging suture on the needle package 80. This detector unit and procedure may be used at a variety of locations; however, preferably they are used at station 50, immediately after the suture has been wound onto the needle package 80.

With particular reference to FIG. 22, detector unit 580 includes mounting bracket 582, sensor 584 and a pair of guide members 586a and 586b, and sensor 584 includes a pair of sensor elements 584a and 584b. Sensor elements 584a and 584b are mounted on bracket 582 and are opposite each other, and these sensors form an LED and phototransistor or photodiode combination. Guide members 586a and 586b are also mounted on bracket 582, extend outward therefrom and form a v-shaped guide. Preferably, detector unit 580 is mounted in a fixed position closely adjacent the outer circumference of packaging disc 36.

In use, as a needle package 80 moves toward detector unit 580, any suture hanging from the package moves between guide members 586a and 586b and is guided by those members so that the suture moves between senor elements 584a and 584b, breaking the light beam of the LED/photoreceptor combination. With this arrangement, if the light beam of sensor 584 is not broken during a given work cycle, this indicates that the package 80 moving past the sensor in this work cycle does not have any hanging sutures. In contrast, if the light beam of sensor 584 is broken during a given work cycle, this indicates that the package 80 moving past the sensor in this work cycle does have a hanging suture.

FIG. 22 illustrates a routine 600 for detecting a hanging suture on the needle package 80. This procedure may be used at a variety of locations; however, preferably it is used at station 50, immediately after the suture has been wound onto the needle package 80. The first step 602 in this routine is to determine whether a motor, which is used to rotate the needle package 80 to wind the suture, is off. If this motor is off, a timer is reset at step 604 and then the routine proceeds to step 606. If, however, at step 602, the package motor is not off, then routine 600 skips step 604 and proceeds directly to step 606.

At step 606, the control processor determines whether the motor for the packaging dial 36 is off. If that motor is not off—indicating that the packaging dial is not finished moving—then routine 600 returns to and repeats step 602. Once the motor for the packaging dial is detected at step 606 as being off, routine 600 moves on to step 610, where the above-mentioned timer is started. This timer may be set, for example, for 0.2 seconds.

From step 610, the routine proceeds to step 612, where the processor checks to determine if the timer has expired. If the timer has not expired, the processor, at step 614, checks to determine if the hanging suture detector is on—that is, if a hanging suture has been detected. If no hanging suture is detected, routine 600 returns to step 602 and continues on from there. If a hanging suture is detected at step 614, then, at step 616, a reject bit is set at the cover-load station, and routine 600 returns to step 602.

Routine 600 continues in the above-discussed manner until the time delay period, tested at step 612, is completed. When that time delay is finished, routine 600 proceeds from step 612 to step 620. Step 620, like step 614, is used to determine whether a hanging suture has been detected. Steps 620 and 614 are similar in that, at both steps, if no hanging suture is detected, the routine returns to step 602. Steps 620 and 614 are different in that, if a hanging suture is detected at step 620, the reject bit is set at step 622 at the needle detect station, rather than at the cover load station.

This time delay is used to insure that the reject bit is set in the appropriate package status word. To elaborate, in the operation of packaging mechanism 16, a respective one status word is associated with each package on the mechanism. When a package moves from one station to another station, the status word for that package can be considered as moving with the package from the former station to the latter station.

More precisely, as will be understood by those of ordinary skill in the art, these status words are not actually located at the work stations around mechanism 16, but instead are located in processor memory at locations associated with the work stations. In particular, the package status words are stored in the processor memory at eight memory location, with each of these memory locations being associated with a respective one of the work stations 42, 44, 34, 46, 50, 52, 54 and 56.

When a particular package is at a given work station, the status word associated with that package is located in the processor memory area associated with that given station; and when a package is moved from one of the work stations to another of the work stations, the status word associated with that package is likewise moved from the processor memory area associated with the former work station to the processor memory area associated with the latter work station.

During the first few cycles through the hanging suture detection routine 600, the package status word associated with the package under inspection is at the memory location associated with the cover-load station. However, just before the package is moved to the needle detect station, the status work associated with the package is transferred to the memory area associated with the needle detect station.

The time delay provided by step 612 is used to insure that if a hanging suture is detected on the package 80 when the status word for the package is at the processor memory area associated with that station, then the reject bit is set in the status word at this processor memory area; but if a hanging suture is detected after the status word for the package has been transferred to the processor memory area associated with the needle detect station 52, then the reject bit is set in the status word at this processor memory area.

Needle Tests

Figure 24:
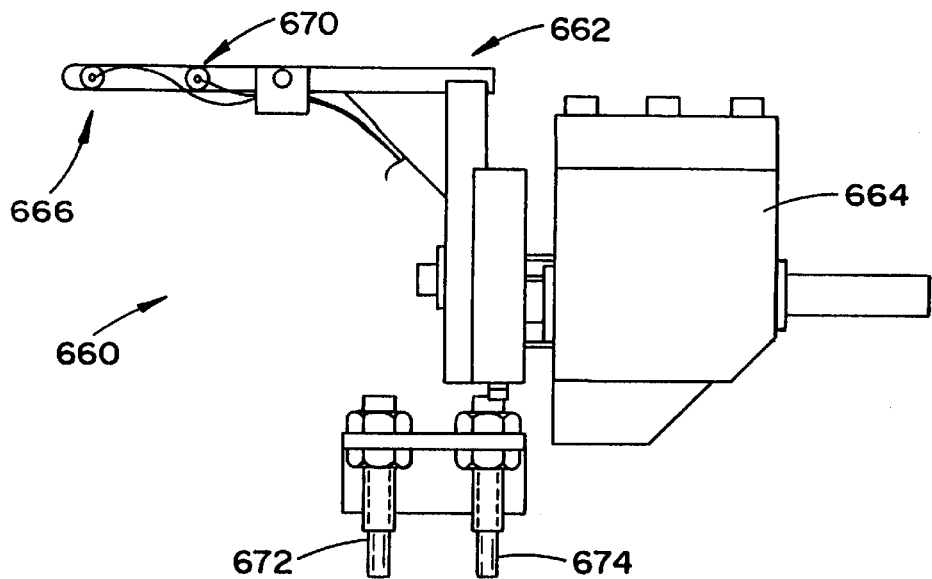
FIGS. 24 and 25 show a detector that may be used to inspect the needle packages for protruding needles.
Figure 25:
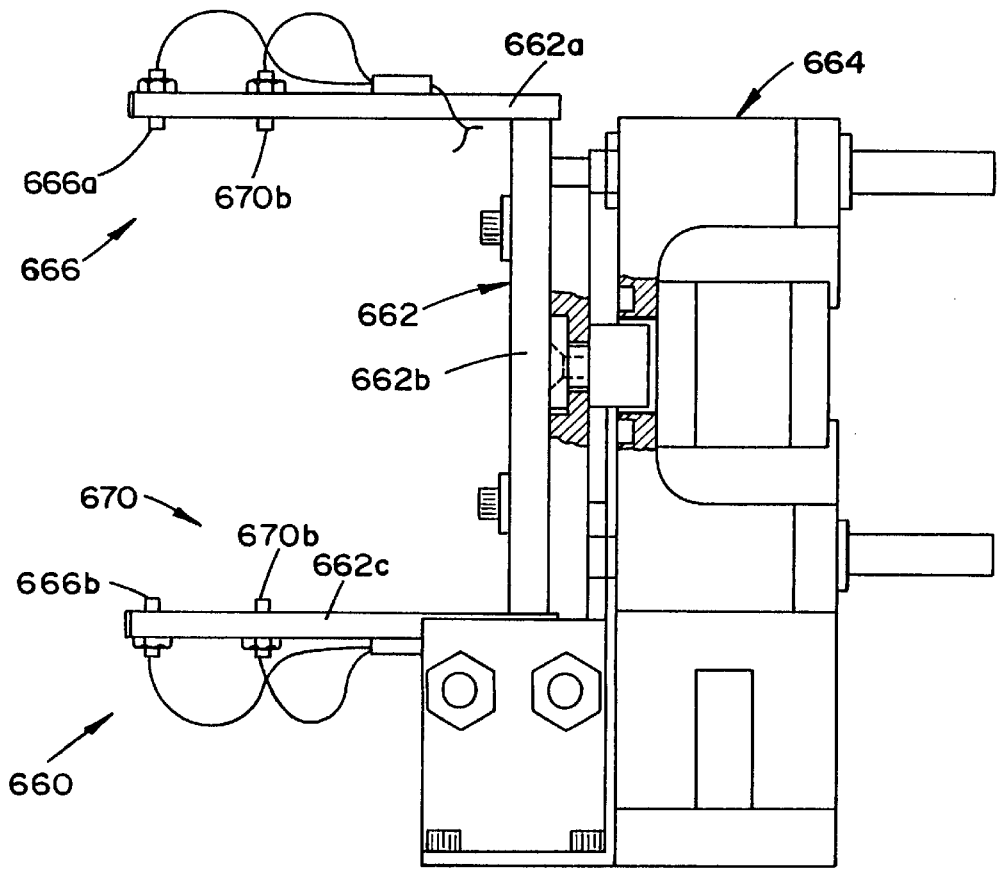
Figure 26:
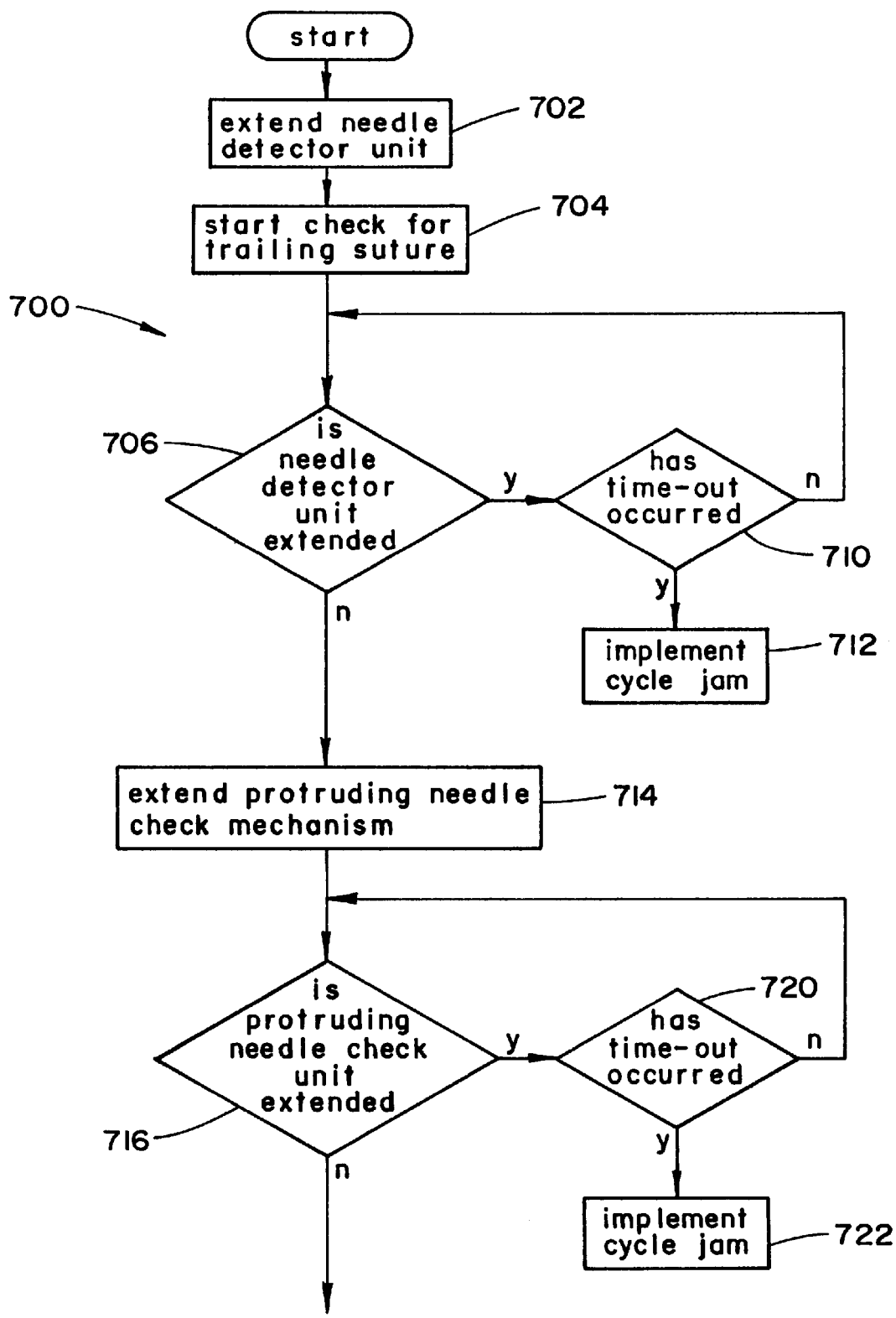
FIGS. 26 and 27 are flow charts outlining a procedure for inspecting the needle packages.
Figure 27:
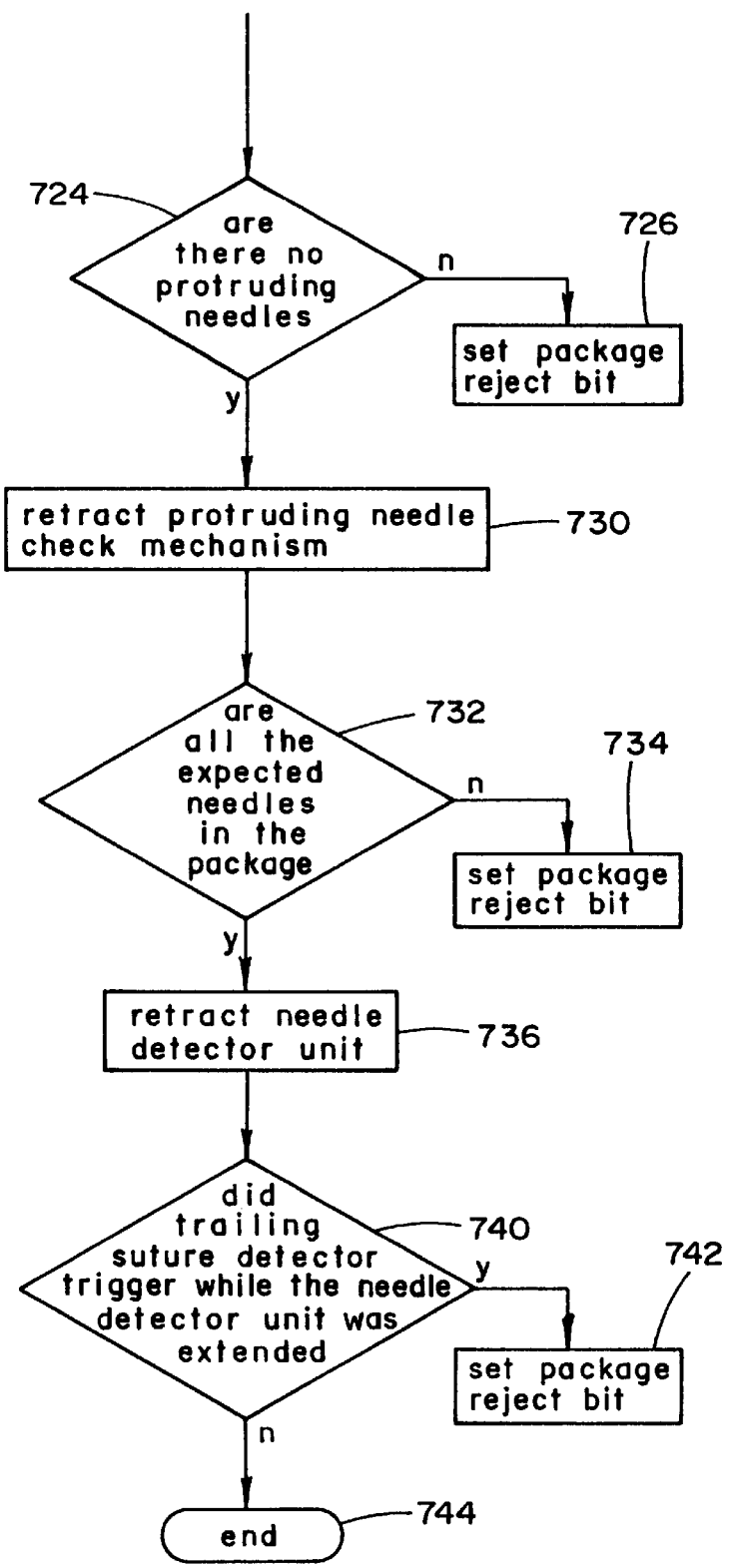

FIGS. 24 and 25 show a unit for detecting whether any needles are protruding from package 80, and FIGS. 26 and 27 show a procedure in which this detector unit is used. Preferably, this detector unit and procedure are used at station 34.

With reference to FIGS. 24 and 25, detector unit 660 includes mounting bracket 662, support member 664, a pair of needle sensors 666 and 670, and a pair of proximity sensors 672 and 674. In turn, needle sensor 666 includes elements 666a and 666b, and needle sensor 670 includes sensor elements 670a and 670b. Mounting bracket 662 has a U-shape, including upper leg 662a, lower leg 662b and intermediate leg 662c. Sensor elements 666a and 670a are mounted on upper leg 662a and sensor elements 666b and 670b are mounted on lower leg 662b directly opposite elements 666a and 670b respectively. Each of the sensors 666 and 670 forms an LED and phototransistor or photodiode combination.

Mounting bracket 662 is supported by support member 664, preferably for sliding movement, toward and away from the support member, between operative and home positions. Any suitable means, such as an air cylinder, may be used to slide mounting bracket 662, and a suitable guide or guides may also be provided to guide that sliding movement of mounting bracket 662. Proximity sensors 672 and 674 are positioned to detect movement of mounting bracket 662 into the operative and home positions respectively.

Detector unit 660 is positioned closely adjacent the outer circumference of packaging disc 36; and after a package 80 has been filled with needles, mounting bracket 662 and sensors 666 and 670 are slid to the operative position, where the sensors are immediately outside that package. If any needle in the package protrudes outside the package, the needle breaks the light beam of the LED/photoreceptor combination. Thus, if the light beam of one of the sensors 666 and 670 is not broken during a given work cycle, this indicates that the package 80 at work station 34 does not have any needles protruding from the package. However, if the light beam of one of the sensors 666 and 670 is broken, this indicates that the package 80 at the work station 34 does have one or more needles protruding from the package. After inspecting package 80 for any protruding needles, mounting bracket 662 and sensors 666 and 670 are returned to the home position.

FIGS. 23 and 24 show a procedure 700 that is employed at station 34 to determine, first, whether the package 80 has all the needles it is supposed to have, and second, whether any of those needles are protruding from the package. The first steps 702 and 704 in this procedure are to extend the needle detector unit and to start checking for any trailing suture on the package. A continuous check is made at step 706 to determine whether the needle detector unit has been extended. If that unit is not fully extended, the system will perform a check at step 710 to determine whether a time-out flag has been generated by the control system, indicating a time-out error. If the time-out flag is generated by the control system, then a cycle jam procedure is implemented at step 712.

If, however, the needle detect unit becomes fully extended before the time-out flag is generated, then the routine proceeds to step 714, and the protruding needle check unit is extended. Here too, a continuous check is made at step 716 to determine whether that unit has been extended. If that unit is not extended at step 716, the system determines, at step 720, whether a time-out flag has been generated. On the one hand, if the time out flag is generated before the protruding needle detector unit is fully extended, then the cycle jam procedure is implemented at step 722. On the other hand, if the protruding needle detector unit is fully extended before the time-out flag is generated, then the routine move on to step 724.

At step 724, unit determines whether any of the needles in package 80 are protruding from that package. If a needle is detected as protruding, then a package reject bit is set at step 726; but if no needle is detected as protruding from the package, then the protruding needle detect unit is retracted at step 730.

From step 730, routine 700 moves on to step 732, where unit determines if package 80 has all the needles it is supposed to have, which, in the preferred embodiment described herein in detail, is eight. If the package does not have the required number of needles, then the package reject bit is set at step 734; however, if the required number of needle are present in the package, the needle detector unit is retracted at step 736. At step 740, the system checks to determine whether any trailing suture was found on package. If a trailing suture was detected, then the package reject bit is set at step 742; while if no trailing suture was found, the routine ends at step 744.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

We claim:

1. A method for packaging surgical needles, in which a plurality of packages are indexed, by moving a package carrier, to a plurality of work stations, each of the work stations including an operating device moveable between home and operating positions, the method comprising the steps of:

moving the operating devices from the home positions to the operating positions to perform operations on the packages, one of said operations including the step of inserting a surgical needle into said package;

finishing said operations;

after the operations are finished, returning the operating devices to the home positions;

each of the work stations generating a respective return home signal when the operating device of the work station returns to the home position of the operating device;

monitoring to determine whether return home signals have been generated indicating that all of the operating devices have returned to their respective home positions; and if return home signals have been generated indicating that all of the operating devices have returned to their respective home positions, moving the package carrier to move each package thereon to another one of the work stations.

2. A method for packaging surgical needles, according to claim 1, further including the step of:

generating an alarm signal if return home signals, indicating that all of the operating devices have returned to their respective home position, are not generated within a defined time period.

3. A method for packaging surgical needles, according to claim 2, wherein the work stations have a work cycle and wherein:

the generating step includes the step of generating the alarm signal if return signals, indicating that all of the operating devices have returned to their respective home positions, are not generated by a time defined relative to the work cycle.

4. A method for packaging surgical needles, according to claim 3, wherein the work cycle has a beginning and an end, and wherein:

the step of moving the operating devices to the operating positions includes the step of moving the operating devices to the operating positions at the beginning of the work cycle;

the step of returning the operating devices to the home positions includes the step of returning the operating devices to the home positions at the end of the work cycle; and the step of generating the alarm signal includes the step of generating the alarm signal if return home signals, indicating that all of the operating mechanisms have returned to their respective home positions, are not generated within a predetermined time after the end of the work cycle.

5. A packaging system for packaging surgical needles, said system comprising:

a plurality of work stations; and a package carrier to hold a plurality of needle receiving packages and to move the needle receiving packages to each of the work stations;

wherein each of the work stations includes i) an operating device moveable between home and operating positions, ii) means to move the operating devices from the home position to the operating position to perform operations on the needle receiving packages, and to return the operating device to the home position after the operation is completed, one of said operations including the insertion of a surgical needle into said package; and iii) means to generate a return home signal when the operating device is returned to the home position;

the needle packaging system further comprising a control system including i) signal receiving means to receive the return home signals nd to determine whether return home signals have been generated indicating that all of the operating devices have returned to their respective home positions, and ii) means to move the package carrier to move each of the needle receiving packages thereon to another one of the work stations if the receiving means receives return home signals from all of said plurality of work stations.

6. A packaging system for packaging surgical needles, according to claim 5, said system further including means for:

generating an alarm signal if return home signals, indicating that all of the operating devices have returned to their respective home position, are not generated within a defined time period.

7. A packaging system for packaging surgical needles, according to claim 6, wherein the work stations have a work cycle and wherein:

the generating means includes means for generating the alarm signal if return signals, indicating that all of the operating devices have returned to their respective home positions, are not generated by a time defined relative to the work cycle.

8. A packaging system for packaging surgical needles, according to claim 7, wherein the work cycle has a beginning and an end, and wherein:

the means to move the operating devices to the operating positions includes i) means for moving the operating devices to the operating positions at the beginning of the work cycle, and ii) means for returning the operating devices to the home positions at the end of the work cycle; and the means for generating the alarm signal includes means for generating the alarm signal if return home signals, indicating that all of the operating mechanisms have returned to their respective home positions, are not generated within a predetermined time after the end of the work cycle.

9. A method for operating a station for transferring needles from a first mechanism to a second mechanism, the second mechanism including a carrier, a plurality of package trays mounted on the carrier and a tray positioning assembly, the method comprising:

moving the carrier to position one of the package trays at the station;

engaging said one of the package trays with the tray positioning assembly;

inserting a plurality of needles from the first mechanism into the one of the package trays, one needle at a time;

operating the tray positioning assembly to move the package tray through a series of discrete positions so that the package tray receives each of said plurality of needles in a respective one of said series of positions;

moving the carrier from a first carrier position to a second carrier position to move said one of the package trays from the station to another location; and after the carrier has reached said second position, moving the tray positioning assembly to a home position.

10. A method according to claim 9, wherein:

the step of moving the carrier from the first carrier position to the second carrier position includes the steps of i) operating a carrier motor to move the carrier, and ii) sensing when the carrier motor is done operating; and the step of moving the tray positioning assembly to the home position includes the step of moving the tray positioning assembly to the home position after sensing when the carrier motor is done operating.

11. A method according to claim 10, wherein the step of moving the carrier from the first carrier position to the second carrier position includes the steps of:

monitoring to determine if the carrier is in the second position; and generating an alarm signal if the carrier is not in the second position.

12. A method according to claim 11, wherein the step of moving the tray positioning assembly to the home position includes the steps of:

monitoring to determine if the tray positioning assembly is in the home position; and generating an alarm signal if the tray positioning assembly is not in the home position.

13. A method according to claim 12, wherein:

the step of monitoring to determine if the tray positioning assembly is in the home position includes the step of monitoring for a predefined period of time to determine if the tray positioning assembly is in the home position; and the step of generating an alarm signal if the tray positioning assembly is not in the home position includes the step of generating an alarm signal if the tray positioning assembly is not in the home position at the end of said predefined period of time.

14. A method according to claim 9, wherein:

the step of operating the tray positioning assembly to move the package tray includes the step of lifting the tray positioning assembly, from a bottom position to a top position, to elevate the package tray through said series of discrete positions; and the step of moving the tray positioning assembly to the home position includes the step of lowering the tray positioning assembly to said bottom position.

15. A packaging system comprising:

a plurality of work stations;

a package carrier to hold a plurality of package trays and to move the package trays to each of the work stations;

means to move the package carrier from a first carrier position to a second carrier position to move each of the package trays on the carrier from one of the work stations to another of the work stations:

wherein the plurality of work stations includes at least a first work station including i) means to insert a plurality of needles into each of the package trays, i) a tray positioning assembly to engage and to move each of the package trays through a series of discrete positions so that each of the package trays receives each of a plurality of needles in a respective one of said series of discrete positions, and iii) means to move the tray position assembly to a home position after the carrier has reached said second position.

16. A packaging system according to claim 15, wherein:

the means to move the carrier includes i) a motor having an operating state to move the carrier, and ii) a sensor to detect when the motor is done operating; and the means to move the tray positioning assembly to the home position includes means to move the tray positioning assemble to the home position after the sensor detects the motor as done operating.

17. A packaging system according to claim 16, wherein the means to move the carrier one step includes:

means to determine if the carrier has moved said one step; and means to generate an alarm signal if the carrier has not moved said one step.

18. A packaging system according to claim 17, wherein the means to move the tray positioning assembly to the home position includes:

means to determine if the tray positioning assembly is in the home position; and means to generate an alarm signal if the tray positioning assembly is not in the home position.

19. A packaging system according to claim 18, wherein:

the means to determine if the tray positioning assembly is in the home position includes means to determine if the tray positioning assembly reaches the home position during a predefined period of time; and the means to generate an alarm signal if the tray positioning assembly is not in the home position includes means to generate an alarm signal if the tray positioning assembly is not in the home position at the end of said predefined period of time.

20. A packaging system according to claim 15, wherein:

the means to move the tray positioning assembly includes means to lift the tray positioning assembly, from the home position to a top position, and then to lower the package tray through said series of discrete positions.

* * * * *